US008541236B2

(12) United States Patent
Heinecke et al.

(10) Patent No.: US 8,541,236 B2
(45) Date of Patent: Sep. 24, 2013

(54) MUTANT APOLIPOPROTEIN A-1 POLYPEPTIDE WITH INCREASED RESISTANCE TO OXIDATION AND REACTIVE CARBONYLS

(75) Inventors: Jay W. Heinecke, Seattle, WA (US); John F. Oram, Seattle, WA (US); Michael N. Oda, Fairfield, CA (US)

(73) Assignees: University of Washington, Seattle, WA (US); The Children's Hospital & Research Center At Oakland, Oakland, CA (US)

( * ) Notice: Subject to any disclaimer, the term of this patent is extended or adjusted under 35 U.S.C. 154(b) by 772 days.

(21) Appl. No.: 11/952,044

(22) Filed: Dec. 6, 2007

(65) Prior Publication Data

US 2008/0234192 A1    Sep. 25, 2008

Related U.S. Application Data

(60) Provisional application No. 60/869,239, filed on Dec. 8, 2006.

(51) Int. Cl.
| | | |
|---|---|---|
| C12N 15/00 | (2006.01) | |
| C12P 21/06 | (2006.01) | |
| A61K 38/00 | (2006.01) | |
| A61K 38/16 | (2006.01) | |
| C07K 14/775 | (2006.01) | |

(52) U.S. Cl.
USPC .......... 435/440; 435/69.1; 514/7.4; 514/21.2; 530/350

(58) Field of Classification Search
None
See application file for complete search history.

(56) References Cited

U.S. PATENT DOCUMENTS

| | | | |
|---|---|---|---|
| 4,643,988 A | 2/1987 | Segrest et al. | |
| 5,211,657 A | 5/1993 | Yamada et al. | |
| 5,256,770 A * | 10/1993 | Glaser et al. | 530/381 |
| 5,824,532 A * | 10/1998 | Barnett et al. | 435/202 |
| 6,265,377 B1 | 7/2001 | Dasseux et al. | |
| 6,617,134 B1 | 9/2003 | Sirtori et al. | |
| 6,953,840 B2 | 10/2005 | Zhu et al. | |
| 2003/0181372 A1 | 9/2003 | Oda et al. | |
| 2004/0067873 A1* | 4/2004 | Dasseux et al. | 514/2 |
| 2005/0222029 A1 | 10/2005 | Bartel et al. | |

FOREIGN PATENT DOCUMENTS

WO        WO 95/25786 A1    9/1995

OTHER PUBLICATIONS

GenBank Accession No. P02647, Dec. 1992.*
Bergt et al., Biochem. J. 346:345-354, 2000.*
Panzenböck et al., Biochim. et Biophys. Acta 1703:171-181, 2005.*
Tsai et al., J. Mol. Biol. 290::253-266, 1999.*
Shuman et al., PNAS 86:9793-9797, 1989.*
Kim et al., "Comparing the effect on protein stability of methionine oxidation versus mutagenesis: steps toward engineering oxidation resistance in proteins", Protein Engineer. 14:343-347, 2001.*
Frank et al., "Apolipoprotein A-I: structure-function relationships", J. Lipid Res. 41:853-872, 2000.*
Shao et al., "Methionine oxidation impairs reverse cholesterol transport by apolipoprotein A-I", PNAS 105:12224-12229, 2008.*
Badimon, J.J., et al., "Role of High Density Lipoproteins in the Regression of Atherosclerosis," *Circulation* 86(Suppl. III):III-86-III-94, 1992.
Barter, P.J., et al., "Antiinflammatory Properties of HDL," *Circulation Research* 95:764-772, 2004.
Baynes, J.W., and S.R. Thorpe, "Forum: Role of Oxidation in Atherosclerosis. Glycoxidation and Lipoxidation in Atherogenesis," *Free Radical Biology & Medicine* 28(12):1708-1716, 2000.
Baynes, J.W., and S.R. Thorpe, "Perspectives in Diabetes. Role of Oxidative Stress in Diabetic Complications. A New Perspective on an Old Paradigm," *Diabetes* 48:1-9, Jan. 1999.
Bergt, C., et al., "Lysine Residues Direct the Chlorination of Tyrosines in YXXK Motifs of Apolipoprotein A-I when Hypochlorous Acid Oxidizes High Density Lipoprotein," *The Journal of Biological Chemistry* 279(9):7856-7866, Feb. 27, 2004.
Bergt, C., et al., "The Myeloperoxidase Product Hypochlorous Acid Oxidizes HDL in the Human Artery Wall and Impairs ABCA1-Dependent Cholesterol Transport," *Proceedings of the National Academy of Sciences USA* 101(35):13032-13037, Aug. 31, 2004.
Blackburn, Jr., W.D., et al., "Apolipoprotein A-I Decreases Neutrophil Degranulation and Superoxide Production," *Journal of Lipid Research* 32:1911-1918, 1991.
Bodzioch, M., et al., "The Gene Encoding ATP-Binding Cassette Transporter 1 Is Mutated in Tangier Disease," *Nature Genetics* 22:347-351, Aug. 1999.
Breslow, J.L., et al., "Isolation and Characterization of cDNA Clones for Human Apolipoprotein A-I," *Proceedings of the National Academy of Sciences USA* 79:6861-6865, Nov. 1982.
Brewer, H.B., et al., "The Amino Acid Sequence of Human APOA-I, an Apolipoprotein Isolated From High Density Lipoproteins," *Biochemical and Biophysical Research Communications* 80(3):623-630, Feb. 14, 1978.
Brot, N., and H. Fliss, "Enzymatic Reduction of Methionine Sulfoxide Residues in Proteins and Peptides," *Methods in Enzymology* 107:352-360, 1984.

(Continued)

*Primary Examiner* — David J Steadman
(74) *Attorney, Agent, or Firm* — Christensen O'Connor Johnson Kindness PLLC

(57) ABSTRACT

In one aspect, the present invention provides isolated oxidation resistant mutant apoA-I polypeptides comprising an amino acid sequence substantially homologous to SEQ ID NO:4, the mutant apoA-I polypeptide comprising a combination of: (1) a conservative amino acid substitution at residue Tyr192; and (2) at least one conservative amino acid substitution at residue Met86, Met112, or Met148, wherein the mutant apoA-I polypeptide is resistant to modification by an oxidizing agent. In another aspect, the invention provides a method of promoting cholesterol efflux activity in a mammalian subject in need thereof, the method comprising the step of administering an effective amount of an oxidation resistant apoA-I agonist to the subject to promote cholesterol efflux.

16 Claims, 14 Drawing Sheets

(56) References Cited

OTHER PUBLICATIONS

Cheung, M.C., et al., "Altered Particle Size Distribution of Apolipoprotein A-I-Containing Lipoproteins in Subjects With Coronary Artery Disease,"*Journal of Lipid Research* 32:383-394, 1991.

Curtiss, L.K., et al. "What Is So Special About Apolipoprotein AI in Reverse Cholesterol Transport?," *Arteriosclerosis, Thrombosis, and Vascular Biology* 26:12-19, 2006.

Daugherty, A., et al., "Myeloperoxidase, a Catalyst for Lipoprotein Oxidation, Is Expressed in Human Atherosclerotic Lesions," *The Journal of Clinical Investigation* 94:437-444, Jul. 1994.

Eisenberg, D., et al., "The Helical Hydrophobic Moment: A Measure of the Amphiphilicity of a Helix," *Nature* 299:371-374, Sep. 23, 1982.

Fitzgerald, M.L., et al., "ABCA1 and Amphipathic Apolipoproteins Form High-Affinity Molecular Complexes Required for Cholesterol Efflux," *Journal of Lipid Research* 45:287-294, 2004.

Fu, X., et al., "Hypochlorous Acid Generated by Myeloperoxidase Modifies Adjacent Tryptophan and Glycine Residues in the Catalytic Domain of Matrix Metalloproteinase-7 (Matrilysin)," *The Journal of Biological Chemistry* 278(31):28403-28409, Aug. 1, 2003.

Fu, X., et al., "Oxidative Cross-Linking of Tryptophan to Glycine Restrains Matrix Metalloproteinase Activity," *The Journal of Biological Chemistry* 279(8):6209-6212, Feb. 20, 2004.

Gillotte, K.L., et al., "Apolipoprotein-Mediated Plasma Membrane Microsolubilization," *The Journal of Biological Chemistry* 274(4):2021-2028, Jan. 22, 1999.

Harrison, J.E., and J. Schultz, "Studies on the Chlorinating Activity of Myeloperoxidase," *The Journal of Biological Chemistry* 251(5):1371-1374, Mar. 10, 1976.

Hazell, L.J., et al., "Presence of Hypochlorite-Modified Proteins in Human Atherosclerotic Lesions," *The Journal of Clinical Investigation* 97(6):1535-1544, Mar. 1996.

Heinecke, J.W., et al., "Dityrosine, a Specific Marker of Oxidation, Is Synthesized by the Myeloperoxidase-Hydrogen Peroxide System of Human Neutrophils and Macrophages," *The Journal of Biological Chemistry* 268(6):4069-4077, Feb. 25, 1993.

Heinecke, J.W., et al., "Superoxide-Mediated Modification of Low Density Lipoprotein by Arterial Smooth Muscle Cells," *The Journal of Clinical Investigation* 77:757-761, Mar. 1986.

Henson, P.M., "Dampening Inflammation," *Nature Immunology* 6(12):1179-1181, Dec. 2005.

Hoffman, M., et al., "Leukocytes and Coronary Heart Disease,"*Atherosclerosis* 172:1-6, 2004.

Kaneider, N.C., et al., "Therapeutic Targeting of Molecules Involved in Leukocyte-Endothelial Cell Interactions," *Federation of European Biochemical Societies Letters* 273:4416-4424, 2006.

Kanellis, P., et al., "Studies of Synthetic Peptide Analogs of the Amphipathic Helix," *the Journal of Biological Chemistry* 255(23):11464-11472, Dec. 10, 1980.

Klebanoff, S.J., "Oxygen Metabolism and the Toxic Properties of Phagocytes," *Annals of Internal Medicine* 93:480-489, 1980.

Lefer, A.M., "Role of the $\beta_2$-Integrins and Immunoglobulin Superfamily Members in Myocardial Ischemia-Reperfusion," *Annals of Thoracic Surgery* 68:1920-1923, 1999.

Lindstedt, K.A., et al., "Proteolysis of the Pericellular Matrix. A Novel Element Determining Cell Survival and Death in the Pathogenesis of Plaque Erosion and Rupture," *Arteriosclerosis, Thrombosis, and Vascular Biology* 24:1350-1358, 2004.

MacIejko, J.J., et al., "Apolipoprotein A-I as a Marker of Angiographically Assessed Coronary-Artery Disease," *New England Journal of Medicine* 309(7):385-389, Aug. 18, 1983.

Martinon, F., et al., "Gout-Associated Uric Acid Crystals Activate the NALP3 Inflammasome," *Nature* 440:237-241, Mar. 9, 2006.

McMillen, T.S., et al., "Expression of Human Myeloperoxidase by Macrophages Promotes Atherosclerosis in Mice," *Circulation* 111:2798-2804, 2005.

Mendez, A.J., et al., "Synthetic Amphipathic Helical Peptides That Mimic Apolipoprotein A-I in Clearing Cellular Cholesterol," *The Journal of Clinical Investigation* 94:1698-1705, Oct. 1994.

Miller, N.E., et al., "The Tromsø Heart-Study. High-Density Lipoprotein and Coronary Heart-Disease: A Prospective Case-Control Study," *Lancet* 1(8019):965-967, May 7, 1977.

Mucchiano, G.I., et al., "Apolipoprotein A-I-Derived Amyloid in Atherosclerotic Plaques of the Human Aorta," *Journal of Pathology* 193:270-275, 2001.

Naiki, H., et al., "Fluorometric Determination of Amyloid Fibrils in Vitro Using the Fluorescent Dye, Thioflavine T," *Analytical Biochemistry* 177:244-249, 1989.

Nakamura, K., et al., "Novel Strategies for the Treatment of Inflammatory Bowel Disease: Selective Inhibition of Cytokines and Adhesion Molecules," *World Journal of Gastroenterology* 12(29):4628-4635, Aug. 7, 2006.

Natarajan, P., et al., "Identification of an Apolipoprotein A-I Structural Element That Mediates Cellular Cholesterol Efflux and Stabilizes ATP Binding Cassette Transporter A1," *The Journal of Biological Chemistry* 279(23):24044-24052, Jun. 4, 2004.

Navab, M., et al., "Apolipoprotein A-I Mimetic Peptides," *Arteriosclerosis, Thrombosis, and Vascular Biology* 25:1325-1331, 2005.

Navab, M., et al., "Human Apolipoprotein AI Mimetic Peptides for the Treatment of Atherosclerosis," *Current Opinion in Investigational Drugs* 4(9):1100-1104, 2003.

Navab, M., et al., "Oral Administration of an Apo A-I Mimetic Peptide.Synthesized From D-Amino Acids Dramatically Reduces Atherosclerosis in Mice Independent of Plasma Cholesterol," *Circulation* 105:290-292, 2002.

Navab, M., et al., "The Role of High-Density Lipoprotein in Inflammation," *Trends in Cardiovascular Medicine* 15(4):158-161, 2005.

Nicholls, S.J., et al., "High-Density Lipoproteins as Therapeutic Targets," *Current Opinion in Lipidology* 16:345-349, 2005.

Nissen, S.E., et al., "Effect of Recombinant ApoA-I Milano on Coronary Atherosclerosis in Patients With Acute Coronary Syndromes," *Journal of the American Medical Association* 290(17):2292-2300, Nov. 5, 2003.

Oda, M.N., et al., "Cysteine Substitutions in Apolipoprotein A-I Primary Structure Modulate Paraoxonase Activity," *Biochemistry* 40:1710-1718, 2001.

Oram, J.F., and J.W. Heinecke, "ATP-Binding Cassette Transporter A1: A Cell Cholesterol Exporter That Protects Against Cardiovascular Disease," *Physiological Reviews* 85:1343-1372, 2005.

Oram, J.F., "HDL Apolipoproteins and ABCA1. Partners in the Removal of Excess Cellular Cholesterol," *Arteriosclerosis, Thrombosis, and Vascular Biology* 23:720-727, 2003.

Panzenböck, U., et al., "Oxidation of Methionine Residues to Methionine Sulfoxides Does Not Decrease Potential Antiatherogenic Properties of Apolipoprotein A-I," *The Journal of Biological Chemistry* 275(26):19536-19544, Jun. 30, 2000.

Peng, D.-Q., et al., "Tyrosine Modificaiton is Not Required for Myeloperoxidase-Induced Loss of Apolipoprotein A-I Functional Activities," *The Journal of Biological Chemistry* 280(40):33775-33784, Oct. 7, 2005.

Pennathur, S., et al., "Human Atheroslcerotic Intima and Blood of Patients With Established Coronary Artery Disease Contain High Density Lipoprotein Damaged by Reactive Nitrogen Species," *The Journal of Biological Chemistry* 279(41):42977-42983, Oct. 8, 2004.

Remaley, A.T., et al., "Apolipoprotein Specificity for Lipid Efflux by the Human ABCAI Transporter," *Biochemical and Biophysical Research Communications* 280:818-823, 2001.

Schreyer, S.A., et al., "Accelerated Atherosclerosis in Mice Lacking Tumor Necrosis Factor Receptor p55," *The Journal of Biological Chemistry* 271(42):26174-26178, Oct. 18, 1996.

Sedlis, S.P., et al., "Plasma Apoproteins and the Severity of Coronary Artery Disease," *Circulation* 73(5):978-986, 1986.

Segrest, J.P., et al., "Amphipathic Helix Motif: Classes and Properties," *Proteins: Structure, Function, and Genetics* 8:103-117, 1990.

Segrest, J.P., et al., "Studies of Synthetic Peptide Analogs of the Amphipathic Helix," *The Journal of Biological Chemistry* 258(4):2290-2295, Feb. 25, 1983.

Segrest, J.P., et al., "The Amphipathic Helix in the Exchangeable Apolipoproteins: A Review of Secondary Structure and Function," *Journal of Lipid Research* 33:141-166, 1992.

Serhan, C.N., and J. Savill, "Resolution of Inflammation: The Beginning Programs the End," *Nature Immunology* 6(12):1191-1197, Dec. 2005.

Shao, B., et al., "Acrolein Impairs ATP Binding Cassette Transporter A1-Dependent Cholesterol Export From Cells Through Site-Specific Modification of Apolipoprotein A-I," *The Journal of Biological Chemistry* 280(43):36386-36396, Oct. 28, 2005.

Shao, B., et al., "Myeloperoxidase: An Inflammatory Enzyme for Generating Dysfunctional High Density Lipoprotein," *Current Opinion in Cardiology* 21:322-328, 2006.

Shao, B., et al., "Myeloperoxidase Impairs ABCA1-Dependent Cholesterol Efflux Through Methionine Oxidation and Site-Specific Tyrosine Chlorination of Apolipoprotein A-I," *The Journal of Biological Chemistry* 281(14):9001-9004, Apr. 7, 2006.

Shao, B., et al., "Tyrosine 192 in Apolipoprotein A-I is the Major Site of Nitration and Chlorination by Myeloperoxidase, but Only Chlorination Markedly Impairs ABCA1-Dependent Cholesterol Transport," *The Journal of Biological Chemistry* 280(7):5983-5993, Feb. 18, 2005.

Tall, A.R., et al., "Regulation and Mechanisms of Macrophage Cholesterol Efflux," *The Journal of Clinical Investigation* 110(7):899-904, Oct. 2002.

Tang, C., et al., "Janus Kinase 2 Modulates the Apolipoprotein Interactions With ABCA1 Required for Removing Cellular Cholesterol," *The Journal of Biological Chemistry* 279(9):7622-7628, Feb. 27, 2004.

Tang, C., et al., "Janus Kinase 2 Modulates the Lipid-Removing But Not Protein-Stabilizing Interactions of Amphipathic Helices With ABCA1," *Journal of Lipid Research* 47:107-114, 2006.

Terkeltaub, R.A., et al., "Apolipoprotein (Apo) E Inhibits the Capacity of Monosodium Urate Crystals to Stimulate Neutrophils," *The Journal of Clinical Investigation* 87:20-26, Jan. 1991.

Van Lenten, B.J., et al., "Influenza Infection Promotes Macrophage Traffic Into Arteries of Mice That Is Prevented by D-4F, an Apolipoprotein A-I Mimetic Peptide," *Circulation* 106:1127-1132, 2002.

Vaughan, A.M., and J.F. Oram, "ABCA1 Redistributes Membrane Cholesterol Independent of Apolipoprotein Interactions," *Journal of Lipid Research* 44:1373-1380, 2003.

Von Eckardstein, A., and G. Assmann, "High Density Lipoproteins and Reverse Cholesterol Transport: Lessons From Mutations," *Atherosclerosis* 137(Suppl.):S7-S11, 1998.

Wang, N., et al., "Specific Binding of ApoA-I, Enhanced Cholesterol Efflux, and Altered Plasma Membrane Morphology in Cells Expressing ABC1," *The Journal of Biological Chemistry* 275(42):33053-33058, Oct. 20, 2000.

Whayne, T.F., et al., "Plasma Apolipoprotein B and VLDL-, LDL-, and HDL-Cholesterol as Risk Factors in the Development of Coronary Artery Disease in Male Patients Examined by Angiography," *Atherosclerosis* 39:411-424, 1981.

Witztum, J.L., and D. Steinberg, "Role of Oxidized Low Density Lipoprotein in Atherogenesis," *The Journal of Clinical Investigation* 88:1785-1792, Dec. 1991.

Zheng, L., et al., "Apolipoprotein A-I is a Selective Target for Myeloperoxidase-Catalyzed Oxidation and Functional Impairments in Subjects With Cardiovascular Disease," *The Journal of Clinical Investigation* 114(4):529-541, Aug. 2004.

Fu, X., et al., "Specific Sequence Motifs Direct the Oxygenation and Chlorination of Tryptophan by Myeloperoxidase," *Biochemistry* 45(12):3961-3971, Mar. 28, 2006.

* cited by examiner

| Helix | AA# | AA Sequence |
|---|---|---|
| | 1 | DEPPQSPWDRVKDLATVYVDVLK |
| | 24 | DSGRDYVSQFEGSALGKQLN |
| Helix 1 | 44 | LKLLDNWDSVTSTFSKLREQLG |
| Helix 2 | 66 | PVTQEFWDNLEKETEGLRQE<u>M</u>S |
| Helix 3 | 88 | KDLEEVKAKVQ |
| Helix 4 | 99 | PYLDDFQKKWQEE<u>M</u>ELYRQKVE |
| Helix 5 | 121 | PLRAELQEGARQKLHELQEKLS |
| Helix 6 | 143 | PLGEE<u>M</u>RDRARAHVDALRTHLA |
| Helix 7 | 165 | PYSDELRQRLAARLEALKENGG |
| Helix 8 | 187 | ARLAE<u>Y</u>HAKATEHLSTLSEKAK |
| Helix 9 | 209 | PALEDLRQGLL |
| Helix 10 | 220 | PVLESFKVSFLSALEEYTKKLN |
| | 242 | TQ |

*Fig.1.*

SEQUENCE LISTING

```
<160> NUMBER OF SEQ ID NOS: 16

<210> SEQ ID NO 1
<211> LENGTH: 897
<212> TYPE: DNA
<213> ORGANISM: Homo Sapiens

<400> SEQUENCE: 1
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg acagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca gaaggtggag ccgctgcgcg     480
cagagctcca gagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg       897

<210> SEQ ID NO 2
<211> LENGTH: 267
<212> TYPE: PRT
<213> ORGANISM: Homo Sapiens

<400> SEQUENCE: 2

Met Lys Ala Ala Val Leu Thr Leu Ala Val Leu Phe Leu Thr Gly Ser
1               5                  10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125
```

```
Gln Lys Lys Trp Gln Glu Glu Met Glu Leu Tyr Arg Gln Lys Val Glu
            130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
                195                 200                 205

Gly Gly Ala Arg Leu Ala Glu Tyr His Ala Lys Ala Thr Glu His Leu
            210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 3
<211> LENGTH: 243
<212> TYPE: PRT
<213> ORGANISM: Homo Sapiens

<400> SEQUENCE: 3

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
            130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
                180                 185                 190

His Ala Lys Ala Thr Glu His Leu Ser Thr Leu Ser Glu Lys Ala Lys
                195                 200                 205

Pro Ala Leu Glu Asp Leu Arg Gln Gly Leu Leu Pro Val Leu Glu Ser
            210                 215                 220
```

```
Phe Lys Val Ser Phe Leu Ser Ala Leu Glu Glu Tyr Thr Lys Lys Leu
225                 230                 235                 240

Asn Thr Gln

<210> SEQ ID NO 4
<211> LENGTH: 198
<212> TYPE: PRT
<213> ORGANISM: Homo Sapiens

<400> SEQUENCE: 4

Leu Lys Leu Leu Asp Asn Trp Asp Ser Val Thr Ser Thr Phe Ser Lys
1               5                   10                  15

Leu Arg Glu Gln Leu Gly Pro Val Thr Gln Glu Phe Trp Asp Asn Leu
            20                  25                  30

Glu Lys Glu Thr Glu Gly Leu Arg Gln Glu Met Ser Lys Asp Leu Glu
        35                  40                  45

Glu Val Lys Ala Lys Val Gln Pro Tyr Leu Asp Asp Phe Gln Lys Lys
    50                  55                  60

Trp Gln Glu Glu Met Glu Leu Tyr Arg Gln Lys Val Glu Pro Leu Arg
65                  70                  75                  80

Ala Glu Leu Gln Glu Gly Ala Arg Gln Lys Leu His Glu Leu Gln Glu
                85                  90                  95

Lys Leu Ser Pro Leu Gly Glu Glu Met Arg Asp Arg Ala Arg Ala His
            100                 105                 110

Val Asp Ala Leu Arg Thr His Leu Ala Pro Tyr Ser Asp Glu Leu Arg
        115                 120                 125

Gln Arg Leu Ala Ala Arg Leu Glu Ala Leu Lys Glu Asn Gly Gly Ala
    130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
            180                 185                 190

Tyr Thr Lys Lys Leu Asn
        195

<210> SEQ ID NO 5
<211> LENGTH: 243
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(243)
<223> OTHER INFORMATION: Wherein X at position 86 and/or 112 and/or
      148 = M or L
<220> FEATURE:
<221> NAME/KEY: MISC_FEATURE
<222> LOCATION: (1)..(243)
<223> OTHER INFORMATION: Wherein X at position 226 = K or R

<400> SEQUENCE: 5

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45
```

```
Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Xaa Ser Lys Asp Leu Glu Glu Val Lys Ala Lys
                 85                  90                  95

Val Gln Pro Tyr Leu Asp Asp Phe Gln Lys Lys Trp Gln Glu Glu Xaa
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Xaa Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Phe
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Xaa Val Ser Phe Leu Ser Ala Leu Glu Glu Tyr Thr Lys Lys Leu
225                 230                 235                 240

Asn Thr Gln

<210> SEQ ID NO 6
<211> LENGTH: 197
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(197)
<223> OTHER INFORMATION: Wherein X at position 43 and/or 69 and/or
      104 = M or L
<220> FEATURE:
<221> NAME/KEY: MISC_FEATURE
<222> LOCATION: (1)..(197)
<223> OTHER INFORMATION: Wherein X at position 182 = K or R

<400> SEQUENCE: 6

Leu Lys Leu Leu Asp Asn Trp Asp Ser Val Thr Ser Thr Phe Ser Lys
 1               5                  10                  15

Leu Arg Glu Gln Leu Gly Pro Val Thr Gln Glu Phe Trp Asp Asn Leu
             20                  25                  30

Glu Lys Glu Thr Glu Gly Leu Arg Gln Glu Xaa Ser Lys Asp Leu Glu
         35                  40                  45

Glu Val Lys Ala Lys Val Gln Pro Tyr Leu Asp Asp Phe Gln Lys Lys
     50                  55                  60

Trp Gln Glu Glu Xaa Glu Leu Tyr Arg Gln Lys Glu Pro Leu Arg Ala
 65                  70                  75                  80

Glu Leu Gln Glu Gly Ala Arg Gln Lys Leu His Glu Leu Gln Glu Lys
                 85                  90                  95

Leu Ser Pro Leu Gly Glu Glu Xaa Arg Asp Arg Ala Arg Ala His Val
            100                 105                 110
```

Asp Ala Leu Arg Thr His Leu Ala Pro Tyr Ser Asp Glu Leu Arg Gln
            115                 120                 125

Arg Leu Ala Ala Arg Leu Glu Ala Leu Lys Glu Asn Gly Gly Ala Arg
        130                 135                 140

Leu Ala Glu Phe His Ala Lys Ala Thr Glu His Leu Ser Thr Leu Ser
145                 150                 155                 160

Glu Lys Ala Lys Pro Ala Leu Glu Asp Leu Arg Gln Gly Leu Leu Pro
                165                 170                 175

Val Leu Glu Ser Phe Xaa Val Ser Phe Leu Ser Ala Leu Glu Glu Tyr
            180                 185                 190

Thr Lys Lys Leu Asn
        195

<210> SEQ ID NO 7
<211> LENGTH: 33
<212> TYPE: PRT
<213> ORGANISM: Artificial Sequence
<220> FEATURE:
<223> OTHER INFORMATION: Synthetic

<400> SEQUENCE: 7

Pro Ala Leu Glu Asp Leu Arg Gln Gly Leu Leu Pro Val Leu Glu Ser
1               5                   10                  15

Phe Lys Val Ser Phe Leu Ser Ala Leu Glu Glu Tyr Thr Lys Lys Leu
            20                  25                  30

Asn

<210> SEQ ID NO 8
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(33)
<223> OTHER INFORMATION: Wherein X at position 18 and/or 30 and/or
      31 = K or R

<400> SEQUENCE: 8

Pro Ala Leu Glu Asp Leu Arg Gln Gly Leu Leu Pro Val Leu Glu Ser
1               5                   10                  15

Phe Xaa Val Ser Phe Leu Ser Ala Leu Glu Glu Tyr Thr Xaa Xaa Leu
            20                  25                  30

Asn

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Asp Trp Leu Lys Ala Phe Tyr Asp Lys Val Ala Glu Lys Leu Lys Glu
1               5                   10                  15

Ala Phe

<210> SEQ ID NO 10
<211> LENGTH: 18
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 2 = W or F
<220> FEATURE:
<221> NAME/KEY: MISC_FEATURE
<222> LOCATION: (1)..(18)
<223> OTHER INFORMATION: Wherein X at position 7 = Y or F

<400> SEQUENCE: 10

Asp Xaa Leu Lys Ala Phe Xaa Asp Lys Val Ala Glu Lys Leu Lys Glu
1               5                   10                  15
Ala Phe

<210> SEQ ID NO 11
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 4 and/or 9 and/or 13
      and/or 15 = K or R

<400> SEQUENCE: 11

Asp Trp Leu Xaa Ala Phe Tyr Asp Xaa Val Ala Glu Xaa Leu Xaa Glu
1               5                   10                  15
Ala Phe

<210> SEQ ID NO 12
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 2 = W or F
<220> FEATURE:
<221> NAME/KEY: MISC_FEATURE
<222> LOCATION: (1)..(18)
<223> OTHER INFORMATION: Wherein X at position 7 = Y or R
<220> FEATURE:
<221> NAME/KEY: MISC_FEATURE
<222> LOCATION: (1)..(18)
<223> OTHER INFORMATION: Wherein X at position 4 and/or 9 and/or 13
      and/or 15 = K or R

<400> SEQUENCE: 12

Asp Xaa Leu Xaa Ala Phe Xaa Asp Xaa Val Ala Glu Xaa Leu Xaa Glu
1               5                   10                  15
Ala Phe

<210> SEQ ID NO 13
<211> LENGTH: 18
<212> TYPE: PRT
<213> ORGANISM: Artificial Sequence
<220> FEATURE:
<223> OTHER INFORMATION: Synthetic

<400> SEQUENCE: 13

Asp Trp Phe Lys Ala Phe Tyr Asp Lys Val Ala Glu Lys Phe Lys Glu
1               5                   10                  15
Ala Phe
```

```
<210> SEQ ID NO 14
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 2 = W or F
<220> FEATURE:
<221> NAME/KEY: MISC_FEATURE
<222> LOCATION: (1)..(18)
<223> OTHER INFORMATION: Wherein X at position 7 = Y or F

<400> SEQUENCE: 14

Asp Xaa Phe Lys Ala Phe Xaa Asp Lys Val Ala Glu Lys Phe Lys Glu
1               5                   10                  15

Ala Phe

<210> SEQ ID NO 15
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 4 and/or 9 and/or 13
      and/or 15 = K or R

<400> SEQUENCE: 15

Asp Trp Phe Xaa Ala Phe Tyr Asp Xaa Val Ala Glu Xaa Phe Xaa Glu
1               5                   10                  15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(18)
<223> OTHER INFORMATION: Wherein X at position 2 = W or F
<220> FEATURE:
<221> NAME/KEY: MISC_FEATURE
<222> LOCATION: (1)..(18)
<223> OTHER INFORMATION: Wherein X at position 7 = Y or F
<220> FEATURE:
<221> NAME/KEY: MISC_FEATURE
<222> LOCATION: (1)..(18)
<223> OTHER INFORMATION: Wherein X at position 4 and/or 9 and/or 13
      and/or 15 = K or R

<400> SEQUENCE: 16

Asp Xaa Phe Xaa Ala Phe Xaa Asp Xaa Val Ala Glu Xaa Phe Xaa Glu
1               5                   10                  15

Ala Phe
```

MUTANT APOLIPOPROTEIN A-1 POLYPEPTIDE WITH INCREASED RESISTANCE TO OXIDATION AND REACTIVE CARBONYLS

CROSS REFERENCE TO RELATED APPLICATION

This application claims the benefit of U.S. Provisional Application No. 60/869,239, filed Dec. 8, 2006.

STATEMENT OF GOVERNMENT LICENSE RIGHTS

This invention was made with U.S. Government support under grant numbers P01HL030086, R01 HL075340, and HL085437 awarded by National Institutes of Health. The U.S. Government has certain rights in this invention.

FIELD OF THE INVENTION

The present invention generally relates to methods and compositions for promoting cholesterol efflux activity in a mammalian subject.

BACKGROUND

It is well established that a correlation exists between elevated levels of serum cholesterol and the development of cardiovascular disease (CVD). Four major circulating lipoproteins have been identified in serum including chylomicrons (CM), very low density (VLDL), low density (LDL) and high density (HDL) lipoproteins. LDL and HDL are the major cholesterol carriers. VLDL and LDL have been shown to be responsible for cholesterol transport from the liver (where it is synthesized or obtained from dietary sources) into extrahepatic tissues in the body, including arterial walls. In contrast, HDL is directly involved in the removal of cholesterol from peripheral tissues, carrying it back to the liver or to other lipoproteins by a mechanism known as reverse cholesterol transport (RCT) (reviewed in Oram, J. F., *Arterioscler. Thromb. Vasc. Biol.* 23:720-727, 2003; Oram, J. F., et al., *Phys. Rev.* 85:1343-1372, 2005). The protective role of HDL has been shown in a number of studies in which high levels of HDL seem to confer cardiovascular protection (see, e.g., Miller, et al., *Lancet* 1(8019):965-968, 1977; Whayne et al., *Atherosclerosis* 39:411-419, 1981). It is hypothesized that high levels of plasma HDL are not only protective against coronary artery disease, but may actually induce regression of atherosclerotic plaques (see, e.g., Badimon, et al., *Circulation* 86(Supp. III):86-94, 1992).

Recent interest in the protective mechanism of HDL has focused on apolipoprotein AI (apoA-I), the major component of HDL. High plasma levels of apoA-I are associated with reduced risk of CVD and less frequent presence of coronary lesions. (See, e.g., Maciejko et al., *N. Engl. J. Med.* 309:385-389, 1983; Sedlis et al., *Circulation* 73:978-984, 1986.) Genetic deficiencies in apoA-I are associated with abnormalities in lipoprotein metabolism that result in low plasma HDL levels, intracellular cholesterol accumulation and premature atherosclerosis. Overexpression of apoA-I in transgenic mice and rabbits increased HDL levels and reduced CVD (von Eckardstein, A., et al., *Atherosclerosis* 137(Supp. S):S7-11, 1998).

Lipid-depleted apoA-I removes excess cholesterol and phospholipids from cells such as macrophages through its interaction with a cell membrane protein called ATP-binding cassette transporter A1 (ABCA1) (Oram, J. F., et al., *Physio. Rev.* 85:1343-1372, 2005). This process has broad specificity for multiple exchangeable HDL apolipoproteins (Remaley, A. T., et al., *Biochem. Biophys. Res. Commun.* 280:818-823, 2001; Segrest, J. P., *J. Lipid Res.* 33:141-166 (1992)). This process is believed to be the rate-limiting step in the generation of mature HDL particles. Studies of human patients and animal models have shown that ABCA1 is cardioprotective. For example, loss-of-function mutations in human ABCA1 cause a severe HDL deficiency syndrome characterized by deposition of cholesterol in tissue macrophages and prevalent CVD. Ablating the ABCA1 gene in mouse macrophages increases atherosclerosis, and increasing ABCA1 expression in mice decreases atherosclerosis. The interaction of apoA-I with ABCA1 or ABCA1-expressing cells elicits several responses involved in exporting cellular cholesterol: removing cholesterol and phospholipids that are transported to the cell surface by ABCA1, stabilizing ABCA1 protein so that it has sustained activity, and stimulating cellular signaling pathways that control ABCA1 activity. In one of these signaling pathways, apoA-I rapidly activates a tyrosine kinase called Janis kinase 2 (JAK2), which promotes the apoA-I binding to ABCA1 necessary for cholesterol removal (Tang, C., et al., *J. Biol. Chem.* 279:7622-7628, 2004). Gene transcription of ABCA1 is highly induced by cellular cholesterol.

Oxidative damage is implicated in the pathogenesis of atherosclerosis, a chronic inflammatory disease. Early atherosclerotic lesions are rich in phagocytic cells, which are predominantly macrophages. Macrophages contribute to the inflammatory process by producing reactive oxygen species such as superoxide and $H_2O_2$ (Klebanoff, S. J., *Ann. Intern. Med.* 93:480-489, 1980). These intermediates can be converted to more the powerful oxidants HOCl and peroxynitrite through a pathway involving myeloperoxidase (MPO), a heme protein released by macrophages via the following reaction: $H_2O_2+Cl^-+H^+ \rightarrow HOCl+H_2O$ (Harrison, J. E., et al., *J. Biol. Chem.* 251:1371-1374, 1976). The physiological importance of this reaction is underlined by the presence of enzymatically active MPO in human atherosclerotic lesions (Daugherty, A., et al., *J. Clin. Invest.* 94:437-444, 1994). Moreover, HOCl-modified lipoproteins have been detected in advanced human atherosclerotic lesions (Hazell, L. J., et al., *J. Clin. Invest.* 97:1535-1544, 1996).

Loss of the ability of apoA-I to remove cholesterol from cells by the ABCA1 pathway is strongly associated with modification of specific amino acid residues in apoA-I (Bergt, C., et al., *Proc. Nat'l Acad. Sci.* 101:13032-13037, 2004; Shao, B., et al., *J. Biol. Chem.* 280:5983-5993, 2005). ApoA-I in human atherosclerotic lesions is modified by acrolein (Shao, B., et al., *J. Biol. Chem.* 280:5983-5993, 2005), a reactive carbonyl generated metabolically and by lipid peroxidation. ApoA-I isolated from atherosclerotic lesions is modified by reactive chlorine and nitrogen species as well as by reactive carbonyls (Pennathur, S., et al., *J. Biol. Chem.* 279:42977-42983, 2004; Shao, B., et al., *J. Biol. Chem.* 279: 7856-7866, 2004). ApoA-I contains four tryptophan residues, and this aromatic amino acid is very sensitive to oxidative damage (Fu, X., et al., *Biochemistry* 45(12):3961-71, 2006; Fu, X., et al., *J. Biol. Chem.* 279(8):6209-12, 2004; Fu, X., et al., *J. Biol. Chem.* 278(31):28403-9, 2003). Thus, oxidation of specific amino acid residues in apoA-I is one mechanism for loss of its biological activities. The underlying factors that may initiate or promote these modifications of apoA-I include inflammation and diabetes, a disorder characterized by elevated levels of reactive carbonyls and a greatly increased risk of atherosclerotic vascular disease (Baynes, J. W., et al.,

*Free Radic Biol Med* 28(12):1708-16, 2000; Baynes J. W. et al., *Diabetes* 48(1): 1-9, 1999).

Animal studies indicate that synthetic amphipathic peptides based on the structural motifs of apoA-I exert potent anti-inflammatory, anti-dyslipidemic and anti-atherogenic effects (Navab, M., et al., *Trends Cardiovasc. Med.* 15(4): 158-61, 2005; Navab, M., et al., *Curr. Opin. Investing Drugs* 4(9):1100-4, 2003). ApoA-I and other apolipoproteins inhibit neutrophil activation (Terkeltaub, R. A., et al., *J. Clin. Invest.* 87(1):20-6, 1991; Blackburn, W. D. Jr., et al., *J. Lipid Res.* 32(12):1911-8, 1991; and Martinon, F., et al., *Nature* 440 (7081):237-41, 2006), indicating that apoA-I or peptides based on the sequence or structure of apoA-I may have therapeutic effects in inflammatory conditions mediated by activated leukocytes (neutrophils, monocytes, macrophages, eosinophils, mast cells and basophils). Leukocytes are of central importance in disorders such as arthritis and other rheumatological conditions as well as a wide range of other acute and chronic inflammatory conditions (Kaneider, N. C., et al., *F.E.B.S. J.* 273(19):4416-24, 2006; Nakamura, K., et al., *World J. Gastroenterol.* 12(29):4628-35, 2006; Serhan, C. N., et al., *Nat. Immunol.* 6(12):1191-7, 2005; Henson, P. M., *Nat. Immunol.* 6(12):1179-81, 2005; and Hoffman, M., et al., *Atherosclerosis* 172(1):1-6, 2004).

Recently, intense interest has developed in using HDL or apoA-I to treat or prevent cardiovascular disease. However, recent studies have shown that cardioprotective effects of HDL and apoA-I may be lost when HDL is oxidatively modified in vivo. The present inventors have determined that mutant apoA-I protein or synthetic peptides resistant to oxidation, reactive carbonyls, or other reactive intermediates promote cholesterol efflux, and therefore may be effective at preventing or treating inflammatory disorders such as arthritis, inflammatory bowel disease, and acute coronary syndrome.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with the foregoing, in one aspect, the present invention provides isolated oxidation resistant mutant apoA-I polypeptides comprising an amino acid sequence substantially homologous to SEQ ID NO:4, the mutant apoA-I polypeptide comprising a combination of: (1) a conservative amino acid substitution at residue Tyr192; and (2) at least one conservative amino acid substitution at residue Met86, Met112, or Met148, wherein the mutant apoA-I polypeptide is resistant to modification by an oxidizing agent.

In another aspect, the present invention provides isolated carbonyl resistant mutant apoA-I polypeptides comprising an amino acid sequence substantially homologous to SEQ ID NO:4, the mutant apoA-I polypeptide comprising a conservative amino acid substitution at residue lysine 226 (Lys 226), to block reactions with acrolein and other reactive carbonyls and amino reactive moieties. In one embodiment, the invention provides one or more conservative amino acid substitutions at residues Lys12, Lys 118, Lys133, Lys195, Lys206, Lys226, Lys238 and Lys 239, or a combination thereof, wherein the mutant apoA-I polypeptide is resistant to modification by a reactive carbonyl such as, for example, malondialdehyde (MDA), or other carbonyls and amino reactive moieties.

In another aspect, the present invention provides at least one oxidation resistant apoA-I agonist polypeptide comprising an amino acid sequence selected from the group consisting of SEQ ID NO:7, SEQ ID NO:9, SEQ ID NO:10, SEQ ID NO:11, SEQ ID NO:13, SEQ ID NO:14, and SEQ ID NO:15.

In another aspect, the invention provides a method of producing an oxidation resistant mutant apoA-I polypeptide comprising the steps of: (a) introducing a conservative amino acid substitution at residue Tyr192 in an amino acid sequence substantially homologous to SEQ ID NO:4; and (b) introducing at least one conservative amino acid substitution at residue Met86, Met112, or Met148, wherein the mutant apoA-I polypeptide is resistant to modification by an oxidizing agent.

In another aspect, the invention provides a method of generating amphipathic alpha-helical peptides at least 70% identical to SEQ ID NOS:3, 4, 5, 6, 7, 8, 9, 10, 11, 12, 13, 14, 15, or 16, or a fragment thereof, comprising L-amino acids and/or D-amino acids that are resistant to functional damage by HOCl, reactive oxygen and nitrogen species, acrolein, reactive carbonyls, and other amino reactive intermediates to exhibit improved cardioprotective and anti-inflammatory activities. The method comprises the step of introducing at least one conservative amino acid substitution, (e.g., a phenylalanine residue for a tyrosine residue, or a leucine residue for a methionine residue), that is resistant to modification by an oxidizing agent such as HOCl or a reactive nitrogen species.

In another aspect, the invention provides a method of producing an oxidation resistant mutant apoA-I polypeptide comprising an amino acid sequence of SEQ ID NO:3 comprising the steps of introducing at least one conservative amino acid substitution at residue tryptophan 8 (Trp8), Trp50, Trp72, Trp108, or a combination thereof, wherein the mutant ApoA-I polypeptide is resistant to modification by an oxidizing agent.

In another aspect, the invention provides a method of promoting cholesterol efflux activity in a mammalian subject in need thereof, the method comprising the step of administering an effective amount of an oxidation resistant apoA-I agonist to the subject to promote cholesterol efflux. In some embodiments, the oxidation resistant apoA-I agonist comprises a polypeptide comprising an amino acid sequence substantially homologous to SEQ ID NO:4, the mutant apoA-I polypeptide comprising a combination of: (1) a conservative amino acid substitution at residue Tyr192; and (2) at least one conservative amino acid substitution at residue Met86, Met112, or Met148, wherein the mutant apoA-I polypeptide is resistant to modification by an oxidizing agent. In some embodiments, the mammalian subject in need thereof is suffering from, or at risk for, cardiovascular disease.

The compositions and methods of the invention are useful for promoting cholesterol efflux effects in vivo in mammalian subjects, including humans suffering from, or at risk for, cardiovascular disease.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates the helical structure of human apoA-I polypeptide provided as SEQ ID NO:3;

DETAILED DESCRIPTION

Figures 2A, 2B, 2C:
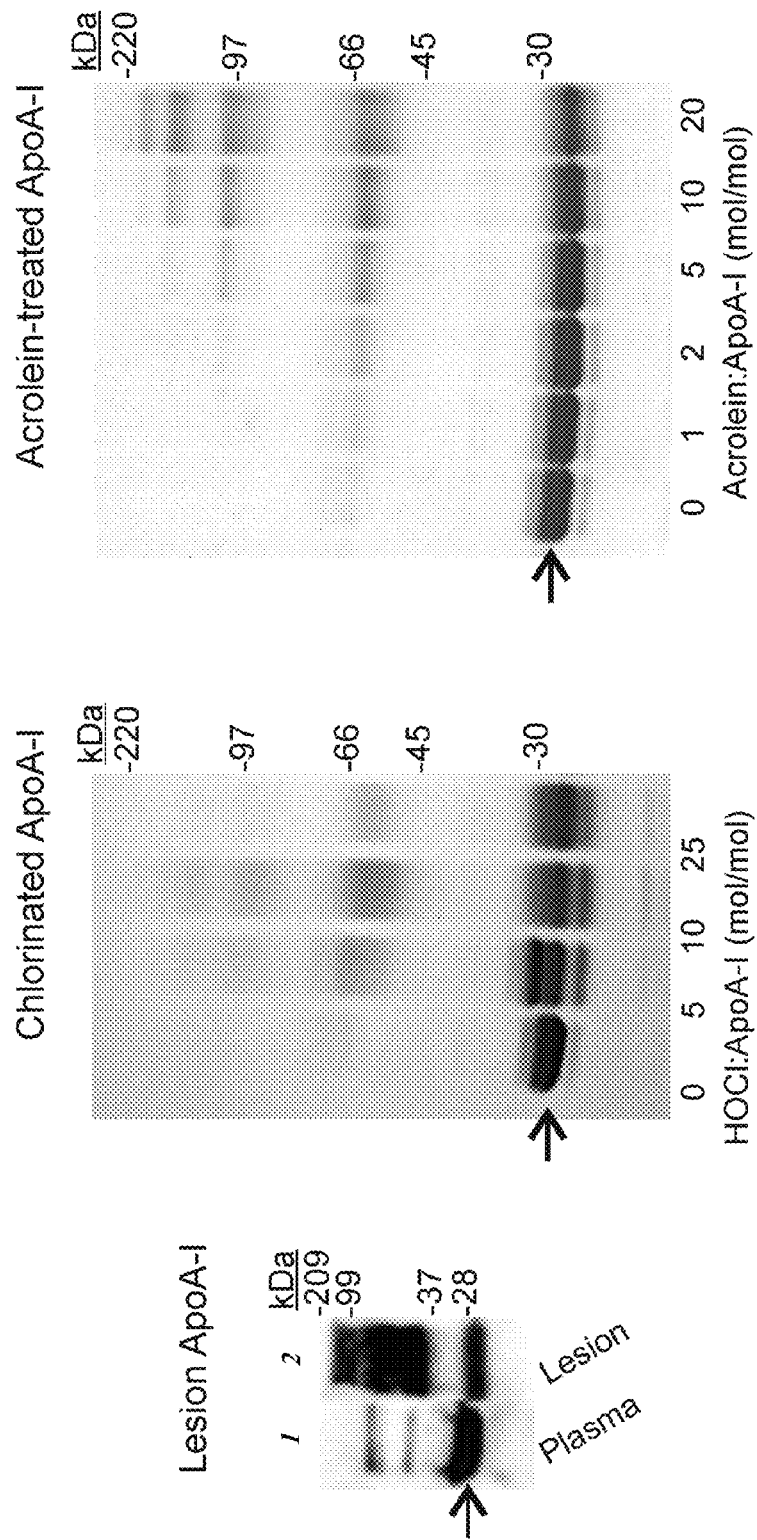
FIG. 2A is an SDS PAGE immunoblot of apoA-I in plasma HDL, shown in lane 1 as compared to HDL isolated from human atherosclerotic lesions shown in lane 2, as described in EXAMPLE 1.
FIG. 2B is an SDS PAGE immunoblot showing that treatment of purified apoA-I with increasing concentrations of HOCl generated higher molecular weight species that were resistant to SDS, as described in EXAMPLE 1.
FIG. 2C is an SDS PAGE immunoblot showing that treatment of purified apoA-I with increasing concentrations of acrolein generated higher molecular weight species that were resistant to SDS, as described in EXAMPLE 1.

Unless specifically defined herein, all terms used herein have the same meaning as they would to one skilled in the art of the present invention. The following definitions are provided in order to provide clarity with respect to the terms as they are used in the specification and claims to describe various embodiments of the present invention.

As used herein, the term "polynucleotide" refers to a chain of nucleotides without regard to length of the chain.

As used herein, the term "polypeptide" refers to a polymer of amino acids without regard to the length of the polymer; thus peptides, oligopeptides and proteins are included in this term. The term "polypeptide" includes polypeptides produced using L- or D-amino acids (the two possible stereoisomers of an amino acid), such as, for example, α-helical peptides or polypeptides.

As used herein, the term "isolated" means a polypeptide or a polynucleotide that has been cloned, synthesized, prepared in a biochemical, bacterial or cellular expression system, or purified from its natural environment.

As used herein, a polynucleotide or fragment thereof is "substantially homologous" to another if, when optimally aligned with the other polynucleotide using BLASTN (Altschul, S. F., et al., *J. Mol. Biol.* 215:403-410, 1990) there is nucleotide sequence identity in at least about 70%, such as at least about 80%, or at least about 90%, or at least about 95%-98% of the nucleotide bases.

As used herein, the term "percent identity" or "percent identical," when used in connection with a biomarker used in the practice of the present invention, is defined as the percentage of amino acid residues in a polypeptide sequence that are identical with the amino acid sequence of apoA-I (such as the amino acid sequence of SEQ ID NO:2, SEQ ID NO:3, or SEQ ID NO:4), after aligning the sequences to achieve the maximum percent identity. When making the comparison, no gaps are introduced into the biomarker sequences in order to achieve the best alignment.

Amino acid sequence identity can be determined, for example, in the following manner. The amino acid sequence of a biomarker (e.g., the amino acid sequence set forth in SEQ ID NO:1) is used to search a protein sequence database, such as the GenBank database using the BLASTP program. The program is used in the ungapped mode. Default filtering is used to remove sequence homologies due to regions of low complexity. The default parameters of BLASTP are utilized.

Preferably, any substitution mutation is conservative in that it minimally disrupts the biochemical properties of the biomarker. Thus, where mutations are introduced to substitute amino acid residues, positively-charged residues (H, K, and R) preferably are substituted with positively-charged residues; negatively-charged residues (D and E) are preferably substituted with negatively-charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys, or Pro. By "hydrophilic" amino acid is meant either Gly, Asn, Gln, Ser, Thr, Asp, Glu, Lys, Arg, or His. This grouping of amino acids can be further subclassed as follows. By "uncharged hydrophilic" amino acid is meant either Ser, Thr, Asn, or Gln. By "acidic" amino acid is meant either Glu or Asp. By "basic" amino acid is meant either Lys, Arg, or His.

Preferably, any substitution mutation is conservative in that it minimally disrupts the biochemical properties of the polypeptide. Conservative substitution tables providing functionally similar amino acids are well known in the art (Henikoff & Henikoff, *Proc. Natl. Acad. Sci. U.S.A.* 89:10915-19, 1992). Thus, where mutations are introduced to substitute amino acid residues, positively-charged residues (H, K, and R) preferably are substituted with positively-charged residues; negatively-charged residues (D and E) are preferably substituted with negatively-charged residues; neutral polar residues (C, G, N, Q, S, and T) are preferably substituted with neutral polar residues; and neutral non-polar residues (A, F, I, L, M, P, V, Y, and W) are preferably substituted with neutral non-polar residues.

As used herein, the term "mutant apoA-I polypeptide" refers to a polypeptide substantially identical to at least 18 consecutive amino acids of SEQ ID NO:2 or SEQ ID NO:3 and comprising at least one amino acid substitution in comparison to the corresponding portion of SEQ ID NO:2 or SEQ ID NO:3.

As used herein, the term "oxidation resistant" in the context of an apoA-I agonist refers to a form of apoA-I polypeptide, suitable apolipoprotein substitute, or an apolipoprotein peptide mimetic that retains biological activity (including but not limited to the direct or indirect promotion of cholesterol efflux), even after exposure to an oxidant, wherein a native amino acid residue that is normally targeted for modification by an oxidant, such as for example, MPO, HOCl, or Acrolein, is substituted for an amino acid that is resistant to targeting/oxidation. In some embodiments of various aspects of the invention, oxidation resistant apoA-I agonists retain cholesterol efflux activity approaching the activity of wild-type apoA-I or synthetic peptide activity, such as at least 50% of wild-type apoA-I activity, (e.g., at least 50%, at least 60%, at least 70%, at least 80%, or at least 90%). The cholesterol efflux activity may be determined using any suitable assay, such as the in vitro assay described in EXAMPLE 4, or with an in vivo assay that monitors atherosclerosis, reverse cholesterol transport, or anti-inflammatory effects (such as preventing leukocyte activation or recruitment into tissue).

As used herein, the term "carbonyl resistant" in the context of an apoA-I agonist refers to a form of apoA-I polypeptide, suitable apolipoprotein substitute or an apolipoprotein peptide mimetic that retains biological activity (including but not limited to the direct or indirect promotion of cholesterol efflux), even after exposure to a reactive carbonyl, wherein a native amino acid residue that is normally targeted for modification by a reactive carbonyl is substituted for an amino acid that is resistant to modification. For example, lysine residues are very reactive with malondialdehyde (MDA), but the positively charged amino acid arginine is not. Thus, a carbonyl resistant apoA-I agonist comprising specific lysine to arginine substitutions are considered resistant to modification by MDA. In some embodiments of the invention, apoA-I agonists are both oxidation resistant and carbonyl resistant.

As used herein, the term "cardiovascular disease" or "CVD" generally refers to heart and blood vessel diseases, including atherosclerosis, coronary heart disease, cerebrovascular disease, and peripheral vascular disease. Cardiovascular disorders are acute manifestations of CVD and include acute coronary syndrome, myocardial infarction, stroke, angina pectoris, transient ischemic attacks, and congestive heart failure. Cardiovascular disease, including atherosclerosis, usually results from the build up of fatty material, inflammatory cells, extracellular matrix, and plaque in artery walls. Clinical symptoms and signs indicating the presence of CVD include one or more of the following: chest pain and other forms of angina, shortness of breath, sweatiness, Q waves or inverted T waves on an EKG, a high calcium score by CT scan, at least one stenotic lesion on coronary angiography or carotid angiography, occlusion of the carotid artery, or heart attack.

It is known that high density lipoprotein ("HDL") protects the artery wall against the development of atherosclerosis by removing cholesterol from cells of the artery wall (see, e.g., Oram, J. F., *Arterioscler. Thromb. Vasc. Biol.* 23:720-727, 2003). Some studies have indicated that HDL may directly protect against atherosclerosis by removing cholesterol from artery wall macrophages (see Tall, A. R., et al., *J. Clin. Invest.* 110:899-904, 2002; Oram, J. F., et al., *Arterioscler. Thromb. Vasc. Biol.* 23:720-727, 2003). It has been shown that Apolipoprotein A-I ("apoA-I"), which accounts for approximately 70% of the total protein in HDL, promotes cholesterol and phospholipid efflux largely by an active transport process mediated by a cell membrane protein called ATP-binding cassette transporter A1 ("ABCA1") (see, e.g., Bodzioch, M., et al., *Nat. Genet.* 22:347-351, 1999). ABCA1 is unique among ABC transporters in that it requires an apolipoprotein partner for transporting substrates. Apolipoproteins modulate multiple processes in the ABCA1 pathway, including removal of ABCA1-transported lipids, stabilization of ABCA1 protein, and activation of signaling pathways important for optimum activity (Oram, J. F., and J. W. Heinecke, *Physiol. Rev.* 85:1343-1372, 2005).

Although increasing HDL levels and cholesterol clearance from arterial macrophages are predicted to reduce cardiovascular disease, it has been observed that oxidation reactions, likely caused by inflammatory conditions in the artery wall, severely impairs cholesterol efflux by the ABCA1 pathway (Bergt, C., et al., *Proc. Nat'l Acad. Sci.* 101:13032-13037, 2004; Pennathur, S., et al., *J. Biol. Chem.* 279:42977-42983, 2004; Zheng, L., et al., *J. Clin. Invest.* 114:529-541, 2004). Consistent with these observations, it is known that HDL is chlorinated in human atherosclerotic lesions and in the blood of subjects with established coronary artery disease. Therefore, the present inventors have proposed that site-specific modifications of apoA-I by reactive intermediates modify apoA-I and impair reverse cholesterol transport and other biological functions of apoA-I. Thus, oxidation-induced and reactive carbonyl-induced modifications of apoA-I may be of central importance in atherogenesis.

It has been shown that an 18 amino-acid peptide analog of the type of amphipahtic a-helices found in apolipoproteins removes cholesterol and phospholipids from cholesterol-loaded cells (Mendez, A. J., et al., *J. Clin. Invest.* 94:1698-1705, 1994). A recent study has confirmed that this and similar peptides containing either alpha-helical peptides composed of either L- or D-amino acids, including SEQ ID NO:9 and SEQ ID NO:13, can remove cellular cholesterol and phospholipids by the ABCA1 pathway. These peptides mimic the effects of apoA-I by removing cellular lipids through ABCA1, directly interacting with ABCA1, stabilizing ABCA1 protein, and activating the signaling molecule JAK2 (Tang, C., et al., *J. Lipid Res.* 47:107-114, 2006). It has also been shown that HOCl impairs the lipid removal activity of one of these peptides, 2F (SEQ ID NO:9), see FIG. 9C and TABLE 1. Thus, the potential therapeutic benefits of these peptides when administered in vivo may be substantially impaired by the same oxidation reactions that impair apoA-I.

The present inventors have now generated engineered apoA-I mutants that are resistant to functional damage by HOCl, acrolein, malondialdehyde and other reactive intermediates and have shown that these oxidation and/or carbonyl resistant apoA-I mutants are capable of promoting cholesterol efflux activity and therefore are expected to have improved atheroprotective and anti-inflammatory activities. Accordingly, in one aspect, the invention provides methods of generating apoA-I mimetic peptides that are resistant to oxidative and/or carbonyl damage and thus have improved therapeutic benefits.

Figures 5A, 5B, 5C:
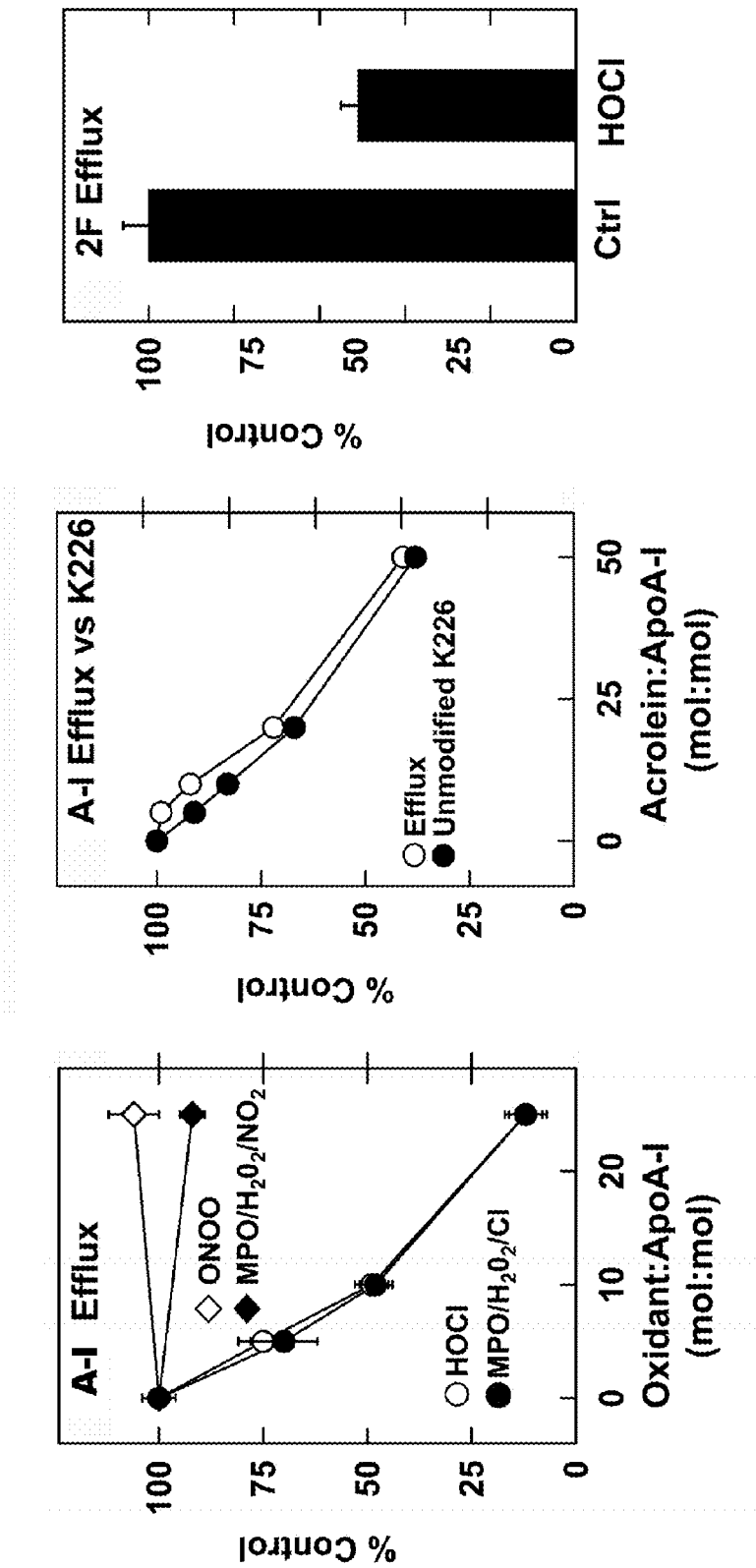
FIG. 5A graphically illustrates the effect of treatment of apoA-I wherein increasing concentrations of HOCl progressively and extensively impaired the cholesterol efflux activity of apoA-I, and the reduction in activity was proportional to the degree of chlorination of tyrosine 192, however MPO-mediated nitration of apoA-I had only a small inhibitory effect on cholesterol efflux activity, as described in EXAMPLE 4.
FIG. 5B graphically illustrates the effect of treatment of apoA-I wherein increasing concentrations of acrolein progressively impaired the cholesterol efflux activity of apoA-I, and the impairment was highly correlated to the adduction of lysine 226, as described in EXAMPLE 4.
FIG. 5C graphically illustrates the effect of treatment of apoA-I peptide mimetic 2F (SEQ ID NO:8) wherein a 25 molar excess of HOCl significantly reduced its ABCA1 dependent cholesterol efflux activity in comparison to untreated 2F peptide, as described in EXAMPLE 4.

As described herein, it has been observed that specific sites in apoA-I must be oxidatively modified to cause it to lose its cardioprotective effects. In the present invention, mutant versions of apoA-I have been made to produce oxidation resistant apoA-I proteins for use as therapeutics in the treatment and/or prevention of cardiovascular disease and inflammatory disease. SEQ ID NO:1 is the polynucleotide sequence encoding wild type human apoA-I protein (SEQ ID NO:2), found under GenBank Accession No. NM_000039.1 (Breslow, J. L., et al., *Proc. Natl. Acad. Sci.* 79(22):6861-6865, 1982). Human apoA-I is synthesized as a 267 amino acid precursor in the cell (SEQ ID NO:2). This pre-pro-apolipoprotein is processed by N-terminal cleavage first intracellularly where 18 amino acids are lost and then with a further cleavage of 6 amino acids in the plasma or the lymph by the activity of specific proteases, to yield the mature form of wild type human apoA-I that is 243 amino acid polypeptide (SEQ ID NO:3), shown in FIG. 1 (see Brewer, et al., *Biochem. Biophys. Res. Commun.* 80:623-630, 1978). It has been shown that after the combination of Tyr192 chlorination and methionine oxidation of apoA-I, at least one of the methionine residues Met86, Met112, or Met148 is necessary for depriving apoA-I of its ABCA1-dependent cholesterol transport activity, as shown in FIGS. 7A-C, FIGS. 8A-9B, and described in EXAMPLES 4, 7, and 8. It has also been observed that oxidation of small apolipoprotein-mimetic amphipathic alpha-helical peptides reduced their ability to remove cholesterol from cells, as shown in FIG. 5C and described in EXAMPLE 4. It has further been demonstrated that conservative amino acid substitutions in the apoA-I polypeptide at specific sites produces oxidation resistant apoA-I agonists that retain the ability to remove cholesterol in the presence of oxidizing agents, as described herein, shown in FIGS. 8A-9C, and described in EXAMPLES 6-8. The oxidation resistant apoA-I agonists described herein may be used as therapeutics in the treatment and/or prevention of cardiovascular disease and inflammatory disease.

In accordance with the foregoing, in one aspect, the present invention provides oxidation resistant mutant apoA-I polypeptides comprising an amino acid sequence substantially homologous to helix 1 to 10 of the mature human apoA-I polypeptide (SEQ ID NO:4) and comprising a combination of: (1) a conservative amino acid substitutional residue Tyr192, and (2) at least one conservative amino acid substitution at residue Met86, Met112, or Met148, wherein the mutant apoA-I polypeptide is resistant to modification by an oxidizing agent. In one embodiment, the oxidation and/or carbonyl resistant mutant apoA-I polypeptides further comprise a substitution at the Lys226 residue in helix 10 to render it resistant to acrolein-mediated damage. In another embodiment, the oxidation and/or carbonyl resistant mutant apoA-I contains a substitution in at least one of the residues Lys12, Lys118, Lys133, Lys195, Lys206, Lys226, Lys238, Lys239, or a combination thereof, wherein the mutant apoA-I polypeptide is resistant to modification by acrolein, MDA, or other reactive carbonyls or other amino reactive moieties.

The mature form of apoA-I (SEQ ID NO:3) contains eight 22-mer and two 11-mer tandem amphipathic alpha-helical domains, as shown in FIG. 1. Helix 1 to helix 10 of apoA-I (SEQ ID NO:4) have been shown to function in the removal of cellular cholesterol and phospholipids by the ABCA1 pathway (Natarajan, P., et al., *J. Biol. Chem.* 279:24044-24052, 2004). Studies of synthetic peptides corresponding to each of these helices have shown that helices 1, 9, and 10 have the greatest affinity for phospholipids (Gillotte, K. L., et al., *J. Biol. Chem.* 274:2021-2028, 1999). These results suggest a model whereby the end helices of apoA-I penetrate into the phospholipid bilayer of membranes, thereby promoting the cooperative interactions of other alpha-helical segments with lipids and creating an apolipoprotein/lipid structure that dissociates from membranes. Cross-linking studies have shown that apoA-I directly interacts with ABCA1, and that this interaction is required for removal of lipids (Wang et al., *J. Biol. Chem.* 275:33053-33058, 2000; Fitzgerald, M. L., et al., *J. Lipid. Res.* 45:287-294, 2004).

It has been observed that high levels of apoA-I, the major component of HDL, are associated with reduced risk of cardiovascular disease. However, recent studies have shown that cardioprotective effects of HDL and apoA-I may be lost when HDL is oxidatively modified in vivo. In particular, it has been shown that the powerful oxidant hypochlorous acid (HOCL) alone, or HOCL generated by myeloperoxidase (MPO) system MPO/$H_2O_2$/Cl severely impairs the ability of purified apoA-I to remove the cellular cholesterol and phospholipids by the ABCA1 pathway (Bergt, C. S., et al., *P.N.A.S.* 101: 13032-13037, 2004; Shao, B., et al., *J. Biol. Chem.* 280:5983-5993, 2005).

Figure 8A:
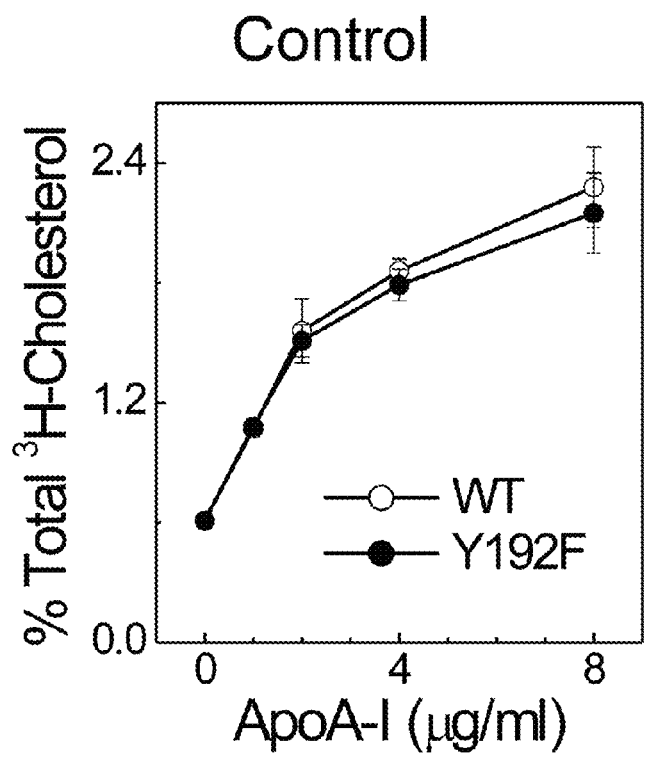
FIG. 8A graphically illustrates the rates of cholesterol efflux activity of apoA-I wild type protein and apoA-I Y192F mutant, as described in EXAMPLE 7.
Figure 8B:
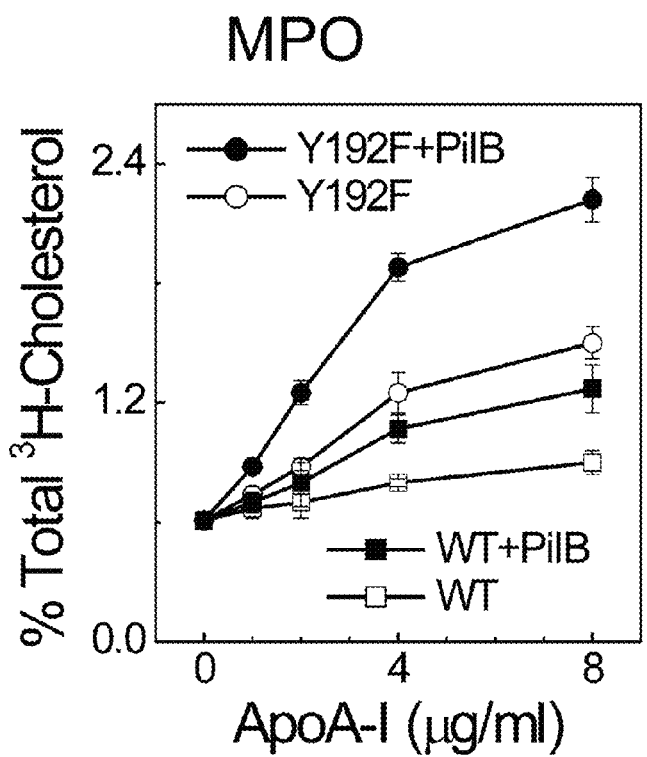
FIG. 8B graphically illustrates the rates of cholesterol efflux activity of wild type apoA-I and the apoA-I Y192F mutant after treatment with MPO or with MPO plus PilB, as described in EXAMPLE 7.

It has previously been shown that MPO or HOCl targets tyrosine residue 192 (Tyr192) when it chlorinates apoA-I, regardless of whether the protein is free or associated with HDL (Bergt et al., supra). However, recent studies of a mutant form of apoA-I in which Phe replaced all seven Tyrosine residues led to the current view that Tyr chlorination is irrelevant to the loss of ABCA-1 dependent cholesterol efflux that occurs when MPO oxidizes apoA-I (Peng, D. Q., et al., *J. Biol. Chem.* 280:33775-33784, 2005). Consistent with the observation by Peng et al., it was observed that an apoA-I Tyr192Phe mutant, which makes the apoA-I residue 192 resistant to chlorination, had only a small protective effect against apoA-I inactivation by either HOCL or the MPO system, as shown in FIGS. 8A and 8B and described in more detail in EXAMPLE 7.

It has now been observed that conversion of Tyr192 to Phe in apoA-I is not by itself enough to render apoA-I resistant to modification by oxidizing agents, but that protection against oxidation of one or more of the 3 methionines in apoA-I is also required to prevent oxidation induced loss of ABCA1 activity. As shown in FIGS. 8A-9C and described in EXAMPLES 7 and 8, a synergistic effect has been discovered indicating that Tyr192 chlorination in combination with Met oxidation are necessary for depriving apoA-I of its cholesterol efflux activity.

In accordance with this aspect of the invention, the mutant apoA-I polypeptides are substantially homologous to helix 1 through helix 10 of wild-type apoA-I (SEQ ID NO:4) and comprise a combination of: (1) a conservative amino acid substitution at residue Tyr192; and (2) at least one conservative amino acid substitution at Met86, Met112, or Met148, wherein the mutant apoA-I polypeptide is resistant to modification by an oxidizing agent.

The conservative amino acid substitution at residue Tyr192 may be any conservative substitution, such as Phe, Leu, Ala, Isoleucine or Val, and at the one or more methionine residues, such as Leu, Isoleucine, Ala, Phe, or Val, that are resistant to oxidation by MPO, HOCl, or Acrolein. The resulting apoA-I mutant polypeptides of the invention mimic apoA-I function and activity, however, unlike native apoA-I, they are resistant to oxidation and retain cholesterol efflux activity in the presence of oxidants such as MPO, HOCl, or Acrolein. In some embodiments, the mutant apoA-I has at least 50% of wild type apoA-I activity in an in vitro cholesterol efflux activity, such as the assay described in EXAMPLE 4. In some embodiments, the mutant is resistant to a reduction in cholesterol efflux activity after exposure to an oxidizing agent, and retains at least 50% of its activity.

In one embodiment, the mutant apoA-I polypeptide comprises a Tyr192Phe substitution and at least one conservative amino acid substitution at a methionine residue, as shown below in TABLE 1. In one embodiment, the invention provides an apoA-I mutant polypeptide that is substantially homologous to mature apoA-I (SEQ ID NO:3) and comprises a Tyr192Phe mutation and at least one Met to Leu substitution at Met86, Met112, or Met148. In another embodiment, the invention provides an apoA-I mutant polypeptide that is substantially homologous to mature apoA-I (SEQ ID NO:3) and comprises a Tyr192Phe mutation, at least one Met to Leu substitution at Met86, Met112, or Met148, and a conservative substitution at Lys226. In one embodiment, the apoA-I mutant polypeptide comprises SEQ ID NO:5.

In another embodiment, the invention provides an apoA-I mutant polypeptide that is substantially homologous to helix 1 through helix 10 of apoA-I (SEQ ID NO:4) and comprises a Tyr192Phe mutation (numbered with reference to the mature apoA-I SEQ ID NO:3) and at least one Met to Leu substitution at Met86, Met112, or Met148. In another embodiment, the invention provides an apoA-I mutant polypeptide that is substantially homologous to helix 1 through helix 10 of apoA-I (SEQ ID NO:4) and comprises a Tyr192Phe mutation, at least one Met to Leu substitution at Met86, Met112, or Met148, and a conservative substitution at Lys226. In one embodiment, the apoA-I mutant polypeptide comprises SEQ ID NO:6.

In one embodiment, the oxidation resistant apoA-I polypeptide is substantially homologous to SEQ ID NO:4 and comprises Tyr192Phe and at least one of Met86Leu, Met112Leu, and Met148Leu, such as the combination of Tyr192Phe and Met86Leu, the combination of Tyr192Phe, Met86Leu, and Met112Leu, or the combination of Tyr192Phe, Met86Leu, Met112Leu, and Met148Leu.

In one embodiment, the oxidation resistant apoA-I polypeptide is substantially homologous to SEQ ID NO:3 and comprises Tyr192Phe and at least one of Met86Leu, Met112Leu, and Met148Leu, such as the combination of Tyr192Phe and Met86Leu, the combination of Tyr192Phe, Met86Leu, and Met112Leu, or the combination of Tyr192Phe, Met86Leu, Met112Leu, and Met148Leu.

In one embodiment, the invention provides an apoA-I mutant polypeptide that is substantially homologous to helix 1 through helix 10 of apoA-I (SEQ ID NO:4) and comprises a Lys226Arg mutation (numbered with reference to the mature ApoA-I SEQ ID NO:3). In another embodiment, the invention provides an apoA-I mutant polypeptide that is substantially homologous to helix 1 through helix 10 of apoA-I (SEQ ID NO:4) and comprises at least one Lys to Arg substitution at Lys12, Lys118, Lys133, Lys195, Lys206, Lys238, and/or Lys 239.

TABLE 1

| Source | Amino Acid Sequence | Description | SEQ ID NO: |
|---|---|---|---|
| apoA-I mature polypeptide (aa 1-243) | DEPPQSPWDRVKDLATVYVDVLKDSGRDYVSQFEGSALGKQLNLKLLDNWDSVTSTFSKLREQLGPVTQEFWDNLEKETEGLRQEMSKDLEEVKAKVQPYLDDFQKKWQEEMELYRQKVEPLRAELQEGARQKLHELQEKLSPLGEEMRDRARAHVDALRTHLAPYSDELRQRLAARLEALKENGGARLAEYHAKATEHLSTLSEKAKPALEDLRQGLLPVLESFKVSFLSALEEYTKKLNTQ | unmodified | 3 |
| ApoA-I (helix 1-10) (aa 44-240) | LKLLDNWDSVTSTFSKLREQLGPVTQEFWDNLEKETEGLRQEMSKDLEEVKAKVQPYLDDFQKKWQEEMELYRQKVEPLRAELQEGARQKLHELQEKLSPLGEEMRDRARAHVDALRTHLAPYSDELRQRLAARLEALKENGGARLAEYHAKATEHLSTLSEKAKPALEDLRQGLLPVLESFKVSFLSALEEYTKKLN | unmodified | 4 |
| apoA-I mature polypeptide: oxidation resistant (Tyr192F plus Met modification) | DEPPQSPWDRVKDLATVYVDVLKDSGRDYVSQFEGSALGKQLNILKLLDNWDSVTSTFSKIREQLGPVTQEFWDNLEKETEGLRQEXaaSKDLEEVKAKVQPYLDDFQKKWQEEXaaELYRQKVEPLRAELQEGARQKIHELQEKLSPLGEEXaaRDRARAHVDALRTHLAPYSDELRQRLAARLEALKENGGARLAEFHAKATEHLSTLSEKAKPALEDLRQGLLPVLESFXaaVSFLSALEEYTKKLNTQ | wherein Xaa at position 86 and/or 112 and/or 148 = M or L; and Xaa at position 226 = K or R | 5 |
| apoA-I helix 1-10 (aa 44-240) oxidation resistant: (Tyr192F plus Met modification) | LKILDNWDSVTSTFSKIREQLGPVTQEFWDNLEKETEGLRQEXaaSKDLEEVKAKVQPYLDDFQKKWQEEXaaELYRQKVEPLRAELQEGARQKIHELQEKISPLGEEXaaRDRARAHVDALRTHLAPYSDELRQRLAARLEALKENGGARLAEFHAKATEHLSTLSEKAKPALEDLRQGLLPVLESFXaaVSFLSALEEYTKKLN | wherein Xaa at position 43 and/or 69, and/or 104 = M or L; and position 182 = K or R | 6 |
| apoA-I helix 9 and 10 (aa209-240) | Ac-PALEDLRQGLLPVLESFKVSFLSALEEYTKKLN-NH2 | original unmodified | 7 |
| apoA-I helix 9 and 10 oxidation resistant (K to R mutations) | Ac-PALEDLRQGLLPVLESFXaaVSFLSALEEYTXaaXaaLNNH2 | Wherein Xaa at position 18 and/or 30 and/or 31 = K or R | 8 |
| 2F apoA-I mimetic peptide | Ac-DWLKAFYDKVAEKLKEAF-NH2 | unmodified | 9 |
| 2F apoA-I mimetic peptide Oxidation resistant: (W and/or Y mutations) | Ac-DXaaLKAFXaaDKVAEKLKEAF-NH2 | Wherein Xaa at position 2 = W or F and/or Xaa at position 7 = Y or F | 10 |
| 2F apoA-I mimetic peptide Oxidation resistant: (K mutations) | Ac-DWLXaaAFYDXaaVAEXaaLXaaEAF-NH2 | Wherein Xaa at position 4 and/or 9 and/or 13 and/or 15 = K or R | 11 |
| 2F apoA-I mimetic peptide Oxidation resistant: (W and/or Y mutations) and/or (K mutations) | Ac-DXaaLXaaAFXaaDXaaVAEXaaLXaaEAF-NH2 | Wherein Xaa at position 2 = W or F and/or Xaa at position 7 = Y or F; and/or Xaa at position 4, and/or 9 and/or 13 and/or 15 = K or R | 12 |
| 4F apoA-I mimetic peptide | Ac-DWFKAFYDKVAEKFKEAF-NH2 | unmodified original | 13 |

TABLE 1-continued

| Source | Amino Acid Sequence | Description | SEQ ID NO: |
|---|---|---|---|
| 4F apoA-I mimetic peptide Oxidation resistant: (W and/or Y mutations) | Ac-DXaaFKAFXaaDKVAEKFKEAF-NH2 | Wherein Xaa at position 2 = W or F and/or Xaa at position 7 = Y or F | 14 |
| 4F apoA-I mimetic peptide Oxidation resistant: (K mutations) | Ac-DWFXaaAFYDXaaVAEXaaFXaaEAF-NH2 | Wherein Xaa at position 4, and/or 9, and/or 13 and/or 15 = K or R | 15 |
| 4F apoA-I mimetic peptide Oxidation resistant: (W and/or Y mutations) and/or (K mutations) | Ac-DXaaFXaaAFXaaDXaaVAEXaaFXaaEAF-NH2 | Wherein Xaa at position 2 = W or F and/or 7 = Y or F and/or Xaa at position 4, and/or 9, and/or 13 and/or 15 = K or R | 16 |

In another aspect, the present invention provides oxidation resistant apoA-I agonists. In particular, the apoA-I agonists of the invention are mutant forms of apoA-I comprising a polypeptide substantially identical to helix 9-10 (SEQ ID NO:7), or peptide mimetics that directly or indirectly promote cholesterol efflux or inhibit inflammation and are resistant to oxidation and/or carbonyl induced modification. The apoA-I agonists of the invention mimic apoA-I function and activity, however, unlike native apoA-I, they are resistant to oxidation and retain function and activity in the presence of oxidants such as MPO, HOCl, or reactive carbonyls such as acrolein and MDA. Exemplary oxidation resistant apoA-I agonists are shown in TABLE 1 and include SEQ ID NOS:5, 6, 8, and 10-16.

In one embodiment, the apoA-I agonists are apoA-I peptide mimetics. It has been shown that apoA-I peptide mimetics 2F (SEQ ID NO:9) and 4F (SEQ ID NO: 13) mimic apoA-I in removing cell lipids by the ABCA1 pathway, in stabilizing ABCA1 protein, and in stimulating an ABCA1-dependent signaling pathway (Tang et al., *J. Lipid Res.* 47:107-114, 2006). Segrest et al. have synthesized peptides composed of 18 to 24 amino acid residues that share no sequence homology with the helices of apoA-I (Kannelis, et al., *J. Biol. Chem.* 255(3):11464-11472, 1980; Segrest, et al., *J. Biol. Chem.* 258:2290-2295, 1983). The peptide sequences were specifically designed to mimic the amphipathic helical domains of class A exchangeable apolipoproteins in terms of hydrophobic moment (Eisenberg, et al., *Nature* 299:371-374, 1982) and charge distribution (Segrest, et al., *Proteins* 8:103-117, 1990; U.S. Pat. No. 4,643,988). For example, an 18-residue peptide referred to as "18A" or "2F" was designed to be a model class-A alpha helix (Segrest, et al., supra). Based on in vitro studies with peptides described above, a set of "rules" has emerged for designing peptides which mimic the function of apoA-I. However, despite these rules, no one has designed or produced a peptide as active as apoA-I, and none of the peptide "mimetics" described in the literature have been demonstrated to be useful as a drug.

In one aspect, the present invention provides a method of generating amphipathic alpha-helical peptides at least 70% identical to SEQ ID NOS: 3, 4, 5, 6, 7, 8, 9, 10, 11, 12, 13, 14, 15, or 16, or a fragment thereof, comprising L-amino acids and/or D-amino acids that are resistant to functional damage by HOCl, reactive oxygen and nitrogen species, acrolein, reactive carbonyls, and other amino reactive intermediates to exhibit improved cardioprotective and anti-inflammatory activities. The method comprises the step of introducing at least one conservative amino acid substitution (e.g., a phenylalanine residue for a tyrosine residue, or a leucine residue for a methionine residue) that is resistant to modification by an oxidizing agent (such as HOCl or a reactive nitrogen species) into the amphipathic alpha-helical peptide(s). In one embodiment, the present invention provides a method of generating amphipathic alpha-helical peptides at least 70% identical to SEQ ID NOS:8, 10, 11, 12, 14, 15, or 16, comprising L-amino acids and/or D-amino acids that are resistant to functional damage by HOCl, reactive oxygen and nitrogen species, acrolein, reactive carbonyls, and other amino reactive intermediates. The amphipathic alpha-helical peptides of the invention are typically from about 10 amino acid residues in length to about 200 amino acid residues in length, (e.g., from about 10 amino acids to about 100 amino acids in length, or from about 15 amino acids to about 50 amino acids in length, or from about 10 amino acids to about 25 amino acids in length. In some embodiments, the amphipathic alpha-helical peptides are at least 80% (e.g., at least 85%, at least 90%, or at least 95%) identical to a corresponding region of SEQ ID NOS:3, 4, 5, 6, 7, 8, 9, 10, 11, 12, 13, 14, 15, or 16. The amphipathic alpha-helical peptides of the invention will be compared to the prototypic peptides and the non-oxidized peptides for their abilities to remove cellular cholesterol by the ABCA1 pathway after treating the peptides with or without oxidizing agents using the assays described herein. Peptides will be considered oxidation resistant when the treatment with the oxidizing agents causes less than 10% decrease in their cholesterol removal activities. These peptides will then be tested in animal model studies to evaluate their effects on atheroscelerosis.

Previous studies have shown that oral administration to mice of apolipoprotein-mimetic peptide D-4F slightly increased plasma HDL levels, altered arterial macrophage trafficking, enhanced the anti-oxidative/inflammatory activities of HDL, increased reverse cholesterol transport, and reduced atherosclerosis, all processes known to be linked to ABCA1 (Navab, M., et al., *Circulation* 105:290-292, 2002; Navab, M., et al., *Arterioscler. Thromb. Vasc. Biol.* 25:1325-1331, 2005; and Van Lenten, B. J., et al., *Circulation* 106: 1127-1132, 2002). However, it has been observed that apoA-I peptide mimetics, such as 2F (SEQ ID NO:9), are susceptible to oxidation-induced damage leading to loss of cholesterol efflux activity, as shown in FIG. 5C and described in EXAMPLE 4.

Accordingly, in one embodiment, the apoA-I agonists are oxidation resistant apoA-I peptide mimetics comprising a polypeptide substantially homologous to SEQ ID NO:9 (2F) and comprising at least one conservative amino acid substitution at Trp2 and/or at Tyr7. In one embodiment, the apoA-I agonist comprises SEQ ID NO:10. In another embodiment, the oxidation resistant apoA-I agonist is substantially homologous to SEQ ID NO:9 and comprises at least one conservative amino acid substitution at Trp2 and/or Tyr7 and at least one conservative amino acid substitution at Lys4, Lys9, Lys13, or Lys15. In one embodiment, the apoA-I agonist comprises SEQ ID NO:11.

In another embodiment, the present invention provides oxidation resistant apoA-I agonists comprising a polypeptide substantially homologous to SEQ ID NO:13 (4F) and comprising at least one conservative amino acid substitution at Trp2 and/or Tyr4. In one embodiment, the apoA-I agonist comprises SEQ ID NO:14. In another embodiment, the oxidation resistant apoA-I peptide mimetic is substantially homologous to SEQ ID NO:13 and comprises at least one conservative amino acid substitution at Trp2 and/or Tyr4 and at least one conservative amino acid substitution at Lys4, Lys9, Lys13, or Lys15. In one embodiment, the apoA-I agonist comprises SEQ ID NO:16.

In another aspect, the invention provides an isolated polynucleotide comprising a nucleic acid sequence encoding an oxidation resistant apoA-I agonist. In one embodiment, the isolated polynucleotide encodes an apoA-I polypeptide whose amino acid sequence differs from an amino acid sequence of an apoA-I wild type protein (SEQ ID NO:3) or a portion thereof, such as SEQ ID NO:4, by at least one conservative substitution at the Tyr192 position and by at least one conservative substitution at Met86, Met112, or Met148.

The present invention also encompasses a recombinant vector comprising a polynucleotide comprising a nucleic acid sequence encoding an oxidation resistant apoA-I agonist. In some embodiments, the recombinant vector is an expression vector. In some embodiments, the expression vector may be employed in the in vivo expression of apoA-I oxidation resistant agonists in a mammalian subject. In other embodiments, the expression vectors are useful for constructing transgenic animals and gene therapy vectors.

The apoA-I polypeptide agonists may be prepared by site-specific mutagenesis of nucleotides in the cDNA encoding apoA-I (SEQ ID NO:1), or may be prepared by in vitro synthesis using established techniques. For example, the apoA-I agonist polypeptides can be synthesized using standard direct peptide synthesizing techniques (Bodanszky, *Principles of Peptide Synthesis*, Springer-Verlag, Heidelberg, Germany, 1984), such as solid-phase synthesis (see, e.g., Merrifield, *J. Am. Chem. Soc.* 85:2149-54, 1993). Alternatively, a gene encoding apoA-I, such as SEQ ID NO:1, can be subcloned into an appropriate expression vector using well known molecular genetic techniques. Site-specific mutagenesis may be performed using cassette or PCR mutagenesis or other techniques well known in the art, for example, as described in more detail in EXAMPLE 7, to produce DNA encoding the mutant apoA-I polypeptide. The apoA-I polypeptide can then be produced by a suitable host cell such as bacterial, yeast, insect, mammalian, avian and higher plant cells. Any appropriate expression vector (see, e.g., Pouwels, et al., *Cloning Vectors: A Laboratory Manual*, Elsevier, N.Y., 1985) and corresponding suitable host cells can be employed for production of apoA-I polypeptides. Expression hosts include, but are not limited to, bacterial species, mammalian or insect host cell systems including baculovirus systems (see, e.g., Luckow, et al., *Bio/Technology* 6:47, 1988), and established cell lines such as 293, COS-7, C127, 3T3, CHO, HeLa, BHK, etc. For example, apoA-I polypeptides may be purified using ammonium sulfate or ethanol precipitation, gel filtration, hydrophobic interaction chromatography, affinity chromatography, hydroxylapatite chromatography, and high performance liquid chromatography. Art-recognized techniques for the purification of proteins and peptides are set forth, for example, in *Methods in Enzymology*, Vol. 182, "Guide to Protein Purification," Murray P. Deutscher, ed. (1990).

The oxidation resistant apoA-I agonist polypeptides may be modified to increase solubility and/or to maximize the positive or negative charge in order to more closely resemble the segment in the wild type apoA-I protein. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids, or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer, which mimics the natural conformation, charge distribution and function of the parent peptide. Peptides may also be modified by acetylation or amidation.

The resistance of the apoA-I polypeptides to an oxidative agent, such as MPO, HOCl, or Acrolein, may be assessed using an in vitro assay and purified or partially purified proteins. For example, the apoA-I polypeptides may be treated with increasing molar ratios of $H_2O_2$ to protein in the presence of MPO plus NaCl, HOCl, or Acrolein followed by tryptic digestion and analyzed by LC-ESI-MS for the presence of oxidized peptides, as described in EXAMPLE 2 and further described in Shao, B., et al., *J. Biol. Chem.* 280(7): 5983-5993, 2005, incorporated herein by reference.

The cholesterol efflux activity of the apoA-I polypeptides may be assessed using an in vitro assay and purified or partially purified proteins. For example, the apoA-I polypeptides may be assayed in a radiolabeled cholesterol efflux assay from ABCA1 transfected cells, as described in EXAMPLE 4 and further described in Shao, B., et al., *J. Biol. Chem.* 280 (7):5983-5993, 2005.

In another aspect, the present invention provides compositions for promoting cholesterol efflux activity in a mammalian subject in need thereof, comprising a therapeutically effective amount of an oxidation resistant apoA-I agonist and a pharmaceutically acceptable carrier. The oxidation resistant apoA-I agonists can be administered to a subject in need thereof, at therapeutically effective doses to treat or ameliorate conditions associated with reduced cholesterol transport due to oxidative damage, such as atherosclerosis. A therapeutically effective dose refers to the amount of the oxidation resistant apoA-I agonist sufficient to result in amelioration of at least one symptom of the condition, including angina, shortness of breath, diaphoresis, claudication, abdominal pain, diarrhea, joint pain or swelling, and neurological symptoms (weakness, loss of vision, loss of speech, loss of balance, etc.).

Recent studies indicate that HDL is anti-inflammatory and inhibits lipid oxidation in vivo (see, e.g., Navab M., et al., *Trends Cardiovasc. Med.* 15(4):158-161, 2005). These properties may contribute significantly to HDL's ability to inhibit atherosclerosis. Systemic inflammation has been proposed to convert HDL to a dysfunctional form that loses these anti-atherogenic effects (see, e.g., Navab, M., et al., *Trends Cardiovasc. Med.* 15(4):158-161, 2005; Shao, B., et al., *Curr. Opin. Cardiol.* 21(4):322-8, 2006). Loss of anti-inflammatory and antioxidant properties may thus make HDL, apoA-I, or apoA-I mimetic peptides dysfunctional. Moreover, apoA-I inhibits inflammation in mice, animal models of hypercholesterolemia, and in a rabbit model of acute arterial inflammation, indicating that apoA-I or synthetic peptides based on apoA-I may have therapeutic utility in other human inflammatory diseases (Nicholls, S. J., et al., *Curr. Opin. Lipidol.* 16(3):345-9, 2005; Barter, P. J., et al., *Circ. Res.* 95(8):764-72, 2004).

ApoA-I, and other exchangeable apolipoproteins like apoE, inhibit neutrophil activation in response to antibodies and uric acid crystals (Terkeltaub, R. A., et al., *J. Clin. Invest.* 87(1):20-6, 1991; Blackburn, W. D., et al., *J. Lipid. Res.* 32(12):191108, 1991; Martinon, F., et al., *Nature* 440(7081): 237-41, 2006), indicating that apoA-I or peptides based on the sequence or structure of apoA-I may have therapeutic effects in inflammatory conditions mediated by leukocytes. Activated leukocytes (neutrophils, monocytes, macrophages, eosinophils, mast cells and basophils) are of central importance in disorders such as arthritis and other rheumatological conditions as well as a wide range of other acute and chronic inflammatory conditions (Kaneider, N. C., et al., *F.E.B.S. J.* 273(19):4416-24, 2006; Nakamura, K., et al., *World J. Gastroenterol.* 12(29):4628-35, 2006; Serhan, C. N., et al., *Nat. Immunol.* 6(12):1191-7, 2005; Henson, P. M., *Nat. Immunol.* 6(12):1179-81, 2005). Moreover, neutrophil activation and secretion of macrophage proteinases are of central importance in the rupture of atherosclerotic plaques and the acute coronary syndrome (Hoffman, M., et al., *Atherosclerosis* 172 (1):1-6, 2004; Lefer, A. M., *Ann. Thorac. Surg.* 68(5):1920-3, 1999; Lindstedt, K. A., et al., *Arterioscler. Thromb. Vasc. Biol.* 24(8):1350-8, 2004). Therefore, mutant apoA-I protein or synthetic peptides resistant to oxidation, reactive carbonyls, or other reactive intermediates may be more effective at preventing or treating the acute coronary syndrome, myocardial infarction, arthritis, inflammatory bowel disease, and other inflammatory conditions. Short term treatment of humans with established CVD with apoA-I Milano, a cross-linked form of apoA-I, significantly reduces the volume of atherosclerotic lesions in humans (Nissan, S. E., et al., *J.A.M.A.* 290(17):2292-300, 2003). ApoA-I isolated from atherosclerotic lesions is modified by reactive chlorine and nitrogen species as well as by reactive carbonyls (Pennathur, S., et al., *J. Biol. Chem.* 279:42977-42983, 2004; Shao, B., et al., *J. Biol. Chem.* 279:7856-7866, 2004) and this results in loss of the ability of apoA-I to remove cholesterol from cells (Shao B. et al., *Curr. Opin. Cardiol.* 21(4):322-8, 2006; Shao B., et al., *J. Biol. Chem.* 281(14):9001-9004, 2006; Shao, B., et al., *J. Biol. Chem.* 280(7):5983-93, 2005; and Bergt, C., et al., *P.N.A.S.* 101(35):13032-12037, 2004. Accordingly, oxidation and/or carbonyl resistant apoA-I agonist compositions produced in accordance with various embodiments of the present invention may be more effective than apoA-I in the acute or short-term treatment of coronary atherosclerosis or other forms of CVD.

In general, the oxidation resistant apoA-I agonist compositions of the present invention, combined with any other selected therapeutic agents, are suitably contained in a pharmaceutically acceptable carrier. The carrier is non-toxic, biocompatible and is selected so as not to detrimentally affect the biological activity of the apoA-I agonist (and any other therapeutic agents combined therewith). Exemplary pharmaceutically acceptable carriers for peptides are described in U.S. Pat. No. 5,211,657 to Yamada. The oxidation resistant apoA-I agonists described herein may be formulated into preparations in solid, semi-solid, gel, liquid, or gaseous forms such as tablets, capsules, powders, granules, ointments, solutions, depositories, inhalants and injections allowing for oral, parenteral, or surgical administration. The invention also contemplates local administration of the compositions by coating medical devices and the like.

Suitable carriers for parenteral delivery via injectable, infusion, or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed, including synthetic mono- or diglycerides. In addition, fatty acids such as oleic acid find use in the preparation of injectables. The carrier and agent may be compounded as a liquid, suspension, polymerizable or non-polymerizable gel, paste, or salve.

Exemplary formulations can be parenterally administered as injectable dosages of a solution or suspension of the compound in a physiologically acceptable diluent with a pharmaceutical carrier that can be a sterile liquid such as water, oils, saline, glycerol, or ethanol. Additionally, auxiliary substances such as wetting or emulsifying agents, surfactants, pH buffering substances, and the like, can be present in compositions comprising oxidation resistant apoA-I agonists. Additional components of pharmaceutical compositions include petroleum (such as of animal, vegetable, or synthetic origin), for example, soybean oil and mineral oil. In general, glycols such as propylene glycol or polyethylene glycol are preferred liquid carriers for injectable solutions.

The carrier may also comprise a delivery vehicle to sustain (i.e., extend, delay, or regulate) the delivery of the agent(s) or to enhance the delivery, uptake, stability, or pharmacokinetics of the therapeutic agent(s). Such a delivery vehicle may include, by way of non-limiting example, microparticles, microspheres, nanospheres, or nanoparticles composed of proteins, liposomes, carbohydrates, synthetic organic compounds, inorganic compounds, polymeric or copolymeric hydrogels, and polymeric micelles.

For intra-articular delivery, the oxidation resistant apoA-I agonists may be carried in above-described liquid or gel carriers that are injectable, above-described sustained-release delivery vehicles that are injectable, or a hyaluronic acid or hyaluronic acid derivative.

In another aspect, the present invention provides methods for promoting cholesterol efflux activity in a mammalian subject in need thereof, comprising the step of administering an effective amount of an oxidation resistant apoA-I agonist to the mammalian subject to promote cholesterol efflux.

The oxidation resistant apoA-I agonists and pharmaceutical compositions comprising oxidation resistant apoA-I agonists described herein are useful in the methods of this aspect of the invention. apoA-I agonists may be administered in a number of ways depending on whether a local or systemic mode of administration is most appropriate for the condition being treated. For example, by parenteral routes including intramuscular (IM), subcutaneous, intravenous (IV), intra-arterial, inhalational, sublingual, buccal, topical, transdermal, nasal, rectal, vaginal, and other routes of administration that effectively result in dispersal of the delivered agent to a single or multiple sites of intended therapeutic action. Additionally, apoA-I agonists can be administered via introduction of the compositions of the present invention to recirculating blood or plasma. Further, the compositions of the present invention can be delivered by coating or incorporating the compositions on or into an implantable medical device.

The compositions of the present invention may be systemically administered on a periodic basis to a mammalian subject in need thereof at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. In addition, the dosage quantity may be adjusted to account for variation in the frequency of administration and the pharmacokinetic behavior of the delivered agent(s).

In prophylactic applications, the pharmaceutical compositions are administered to a subject susceptible to, or otherwise at risk of, a condition associated with a reduction in cholesterol efflux activity, in an amount sufficient to eliminate or reduce the risk of developing symptoms of the condition. In therapeutic applications, the pharmaceutical compositions are administered to a subject suspected of, or already suffering from, a condition associated with a reduction in cholesterol efflux activity in a therapeutically effective amount sufficient to relieve, or at least partially reduce, the symptoms of the condition. In both prophylactic and therapeutic regimens, compositions comprising oxidation resistant apoA-I agonists may be administered in several dosages until a sufficient therapeutic outcome has been achieved in the subject. Application of the oxidation resistant apoA-I compositions of the present invention may be carried out by a single administration of the composition, or a limited sequence of administrations, or for an extended period of time for treatment of a condition, e.g., atherosclerosis or other cardiovascular disease.

The promotion of cholesterol efflux and anti-inflammatory effects of HDL are characterized by at least one of the following changes as a result of administration of an oxidation and/or carbonyl resistant apoA-I agonist in accordance with the methods of the invention: increases in blood levels of HDL or apoA-I, changes in the resistance of HDL or apoA-I to oxidation or modification by carbonyls in vivo or ex vivo, changes in the level of oxidized HDL in blood (such as carbonylation, chlorination, nitration or oxygenation of apoA-I or of other proteins associated with HDL), cholesterol efflux by the ABCA1 and ABCG1 pathways as assessed using cellular assays, changes in the non-denaturing 2-dimensional electrophoresis of apoA-I in plasma or serum, alterations in the protein composition of HDL (such as PON-1, apoE, apoCI, apoCIII, apoCIV, C3, vitronectin), reduction in lesion size or volume of atherosclerotic lesions as assessed by angiography, magnetic resonance imaging, intravascular ultrasound or CT scan, or changes in serum or plasma inflammatory markers (such as MPO, C-reactive protein, soluble leukocyte adhesion molecules).

The following examples merely illustrate the best mode now contemplated for practicing the invention, but should not be construed to limit the invention.

EXAMPLE 1

This Example demonstrates that apoA-I exists predominantly as a complex in human atherosclerotic lesions.

Methods:

HDL was isolated from human plasma and from human carotid atherosclerotic tissue recovered from surgery by sequential density gradient ultracentrifugation. apoA-I was isolated from isolated HDL or detergent extracts of arterial wall tissue by immunoprecipitation with a rabbit polyclonal Ab monospecific for human apoA-I. (To generate high yields of apoA-I for functional studies, apoA-I is purified from detergent extracts by immunoaffinity chromatography using antibody coupled to CNBr Sepharose 4B. After passage of the tissue extract over the antibody column, apoA-I containing particles are eluted using a pH shift as described in Cheung, M. C., et al., *J. Lipid Res.* 32:383-394, 1991. The ability to extensively wash the magnetic beads and columns allows the purification of apoA-I with minimal contamination with other proteins. This method routinely recovers over 80% of the apoA-I in lesions and yields 50 ug to 100 ug protein from 2 g of tissue.)

In order to analyze the effects of HOCl and acrolein on apoA-I structure, purified apoA-I was treated with a molar ratio of HOCl at mol:mol concentrations of 0, 5, 10, or 25; or with a molar ratio of acrolein at mol:mol concentrations of 0, 1, 2, 5, 10, or 20.

Results:

As shown in FIG. 2A, most of the apoA-I present in lesion-derived HDL appeared as large detergent-resistant higher molecular weight complexes on an SDS PAGE gel, as compared to the apoA-I present in plasma-derived HDL. Moreover, denaturing SDS-PAGE gel analysis revealed that treating purified apoA-I with increasing concentrations of HOCl (FIG. 2B), or acrolein (FIG. 2C), also generated higher molecular weight species that were resistant to SDS. As shown in FIG. 2B and FIG. 2C, some of the higher molecular weight species observed were consistent with apparent MW of dimers (~60 kDa) and trimers (~90 kDa) of apoA-I. In contrast, these higher molecular weight species were not observed when apoA-I was nitrated by either reagent ONOO$^-$ or the complete MPO/$H_2O_2$/$NO_2$ system (data not shown). These results show that the impaired cholesterol efflux activity of HOCl— and acrolein modified apoA-I appears to be strongly associated with complex formation. In contrast, nitration fails to affect the ABCA1 activity of apoA-I, and this is associated with a lack of effect on the apparent molecular mass of apoA-I.

MS analysis performed on the apoA-I samples after HOCl— oxidation failed to uncover any evidence of cross-linking of apoA-I molecules (data not shown), suggesting that conformational changes in apoA-I promoted the formation of non-covalent complexes and/or markedly altered the migration pattern observed of monomeric apoA-I on the SDS PAGE gels. These results support the conclusion that MPO-derived reactive species contribute to the formation of the SDS-resistant complexes observed in HDL isolated from atherosclerotic lesions (shown in FIG. 2A). While not wishing to be bound by theory, the more extensive modifications observed in apoA-I from lesion derived HDL may reflect the combined effects of multiple oxidative processes over an extended time period. These observations suggest that alterations in apoA-I that promote complex formation may have a major impact on the ability of apoA-I to promote cholesterol efflux by the ABCA1 pathway.

EXAMPLE 2

This Example demonstrates that tyrosine 192 (Y192) is the major site of both chlorination and nitration in apoA-I.

Methods:

apoA-I (5 μM) was treated for 1 hour with increasing molar ratios of $H_2O_2$ to protein in the presence of either MPO plus NaCl or MPO plus $NO_2$ at 5:1, 10:1, 25:1, or 50:1 molar ratios for 60 minutes at 37° C. in phosphate buffer. Tryptic digests of apoA-I were then analyzed by LC-ESI-MS and MS/MS and oxidized peptides were detected and quantified using reconstructed ion chromatograms of precursor and product peptides, as described in more detail in Shao, B., et al., J. Biol. Chem. 280(7):5983-5993, 2005.

Figure 3A:
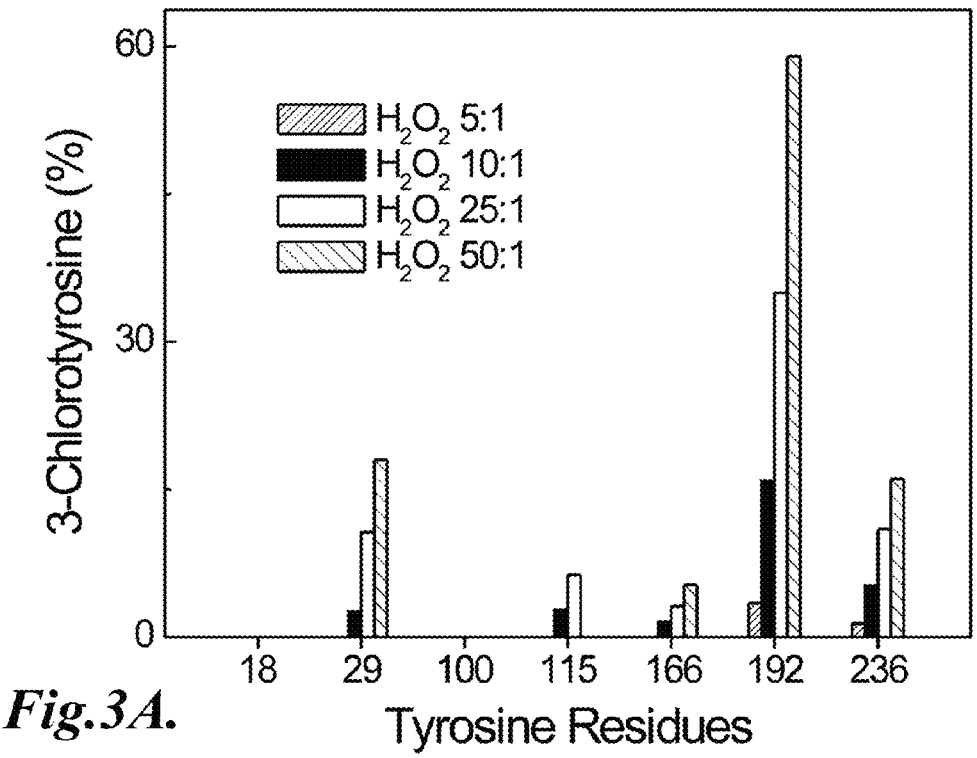
FIG. 3A graphically illustrates the selective chlorination of tyrosine 192 in apoA-I after treatment with increasing molar ratios of $H_2O_2$ to apoA-I protein in the presence of MPO plus NaCl followed by tryptic digestion of apoA-I and detection of oxidized peptides by LC-ESI-MS, as described in EXAMPLE 2.
Figure 3B:
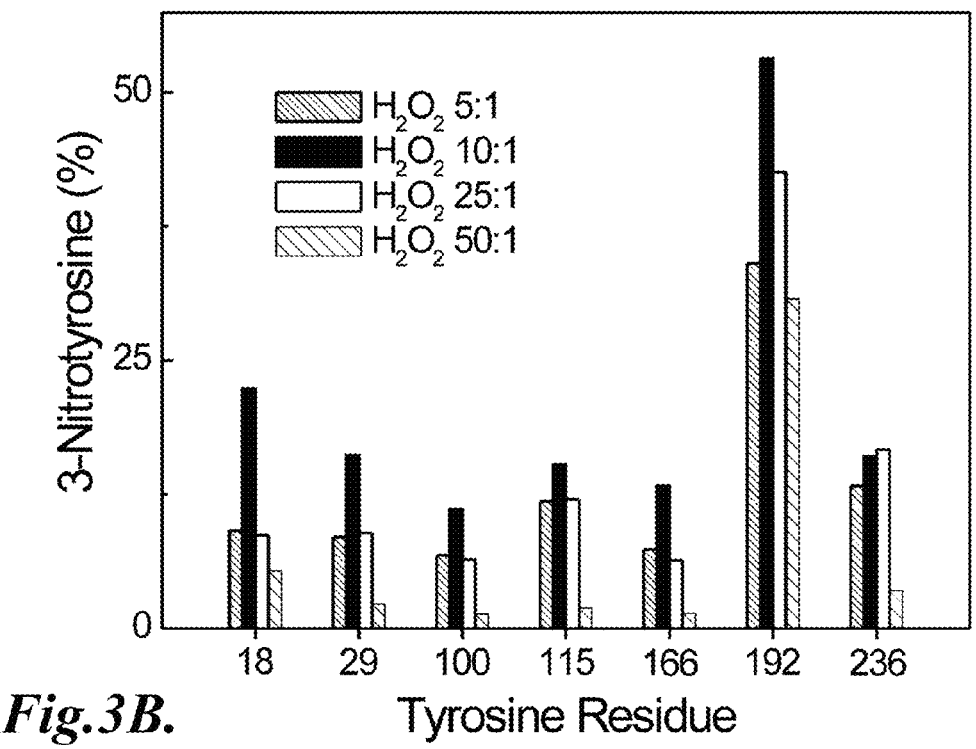
FIG. 3B graphically illustrates the selective nitration of tyrosine 192 in apoA-I after treatment with increasing molar ratios of $H_2O_2$ to apoA-I protein in the presence of MPO plus $NO_2$ followed by tryptic digestion of treated apoA-I and detection of oxidized peptides by LC-ESI-MS, as described in EXAMPLE 2.

Results:

The results shown from chlorination treatment of apoA-I with MPO plus NaCl (FIG. 3A) and nitration of apoA-I with MPO plus $NO_2$ (FIG. 3B) are representative of three independent experiments. These results show that tyrosine 192 (Y192) is the major site of both chlorination and nitration in apoA-I, both of which result in similar extents of Y192 modification.

EXAMPLE 3

This Example demonstrates that treatment of apoA-I with acrolein predominately modifies lysine 226, located near the center of helix 10.

Methods:

Isolation of HDL and apoA-I

Blood was collected from healthy subjects who had fasted overnight and was anticoagulated with EDTA. HDL (density 1.125 g/ml-1.210 g/ml) was prepared from plasma by sequential ultracentrifugation and was depleted of apolipoproteins E and B 100 by heparin-agarose chromatography. apoA-I was purified to apparent homogeneity from HDL.

Acrolein Modification

Reactions with isolated apoA-I (25 uM, 0.7 mg protein/ml), HDL (1 mg protein/ml), or synthetic peptides (100 um) were carried out at 37° C. for 24 h in 50 mM sodium phosphate buffer (pH 7.4) containing 100 uM DTPA. Reactions were initiated by adding acrolein and terminated by adding a 20-fold molar excess (relative to acrolein) of aminoguanidine.

Proteolytic Digestion

Native or acrolein-modified apoA-I or HDL was incubated overnight at 37° C. with a 20:1 ratio (w/w) of endoproteinase Glu-C (from *Staphylococcus aureus* V8), sequencing grade modified trypsin (Promega, Madison, Wis.), or Glu-C/trypsin in 50 mM $NH_4HCO_3$ (pH 7.8). Digestion was halted by acidifying (pH 2-3) with trifluoroacetic acid. LC-ESI-MS analysis was performed as described in Shao, B., et al., J. Biol. Chem. 280(43):3686-3696, 2005, which is incorporated by reference.

Figure 4A:
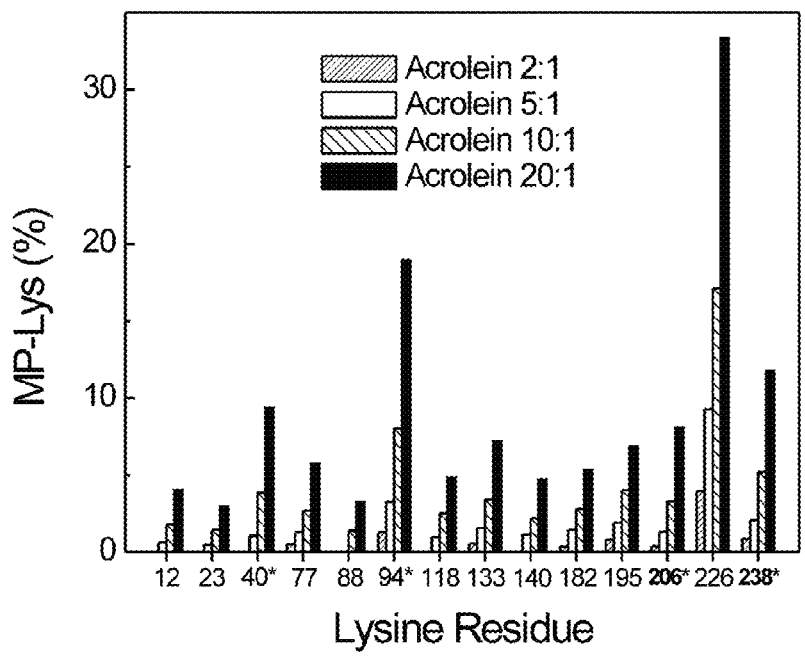
FIG. 4A graphically illustrates the selective modification of lysine 226 in free apoA-I after treatment with increasing molar ratios of acrolein followed by tryptic digestion of treated apoA-I and detection of modified peptides by LC-ESI-MS, as described in EXAMPLE 3.
Figure 4B:
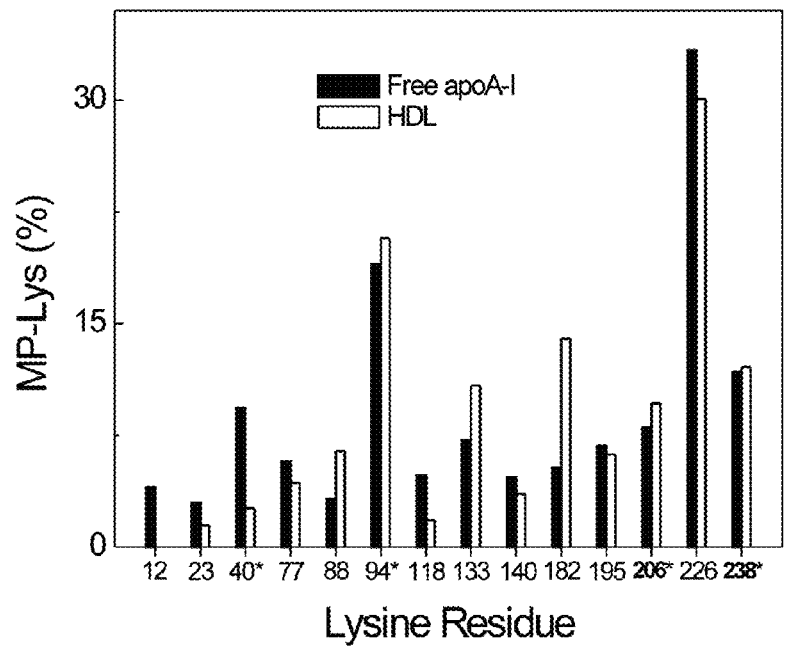
FIG. 4B graphically illustrates the selective modification of lysine 226 in free and HDL-associated apoA-I after treatment with acrolein at a molar ratio of 20:1 (acrolein/protein) followed by tryptic digestion of treated apoA-I and detection of modified peptides by LC-ESI-MS, as described in EXAMPLE 3.

Results:

As shown in FIGS. 4A and 4B, MS/MS analysis of Glu-C digest or tryptic digests of acrolein-modified apoA-I (FIG. 4A) or HDL-associated apoA-I (FIG. 4B) indicated that only a single Lys in each detected peptide (Lys 226 in helix 10) was modified, and that MP-Lys was the major product. It has also been observed in immunohistochemical studies that acrolein adducts co-localize with apoA-I in human atherosclerotic lesions, as described in Shao, B., et al., J. Biol. Chem. 280 (43):3686-3696, 2005, supra.

As shown in Example 4, the conversion of lys226 to MP-Lys is quantitatively associated with inhibition of ABCA1 activity.

EXAMPLE 4

This Example demonstrates that chlorination and acrolein modification, but not nitration, impairs the ability of apoA-I to promote ABCA1 dependent cholesterol efflux.

Methods:

The effect of oxidant treatment of apoA-I on the ability of apoA-I to promote cholesterol efflux from cells via the ABCA1 pathway was measured as follows.

A radiolabeled cholesterol efflux assay from ABCA1-transfected cells was carried out as described in Shao, et al., J. Biol. Chem. 280(7):5983-5993, 2005. Briefly described, baby hamster kidney (BHK) cells expressing mifepristone-inducible human ABCA1 were generated as described in Vaughan, A. M., et al., J. Lipid. Res. 44:1373-1380, 2003. Cellular cholesterol was labeled by adding 1 μCi/ml [$^3$H]cholesterol (Perkin Elmer Life Sciences) to the growth medium. Twenty-four hours later, strong expression of ABCA1 was induced by incubating the cells for 20 h with Dulbecco's modified Eagle's medium containing 1 mg/ml bovine serum albumin and 1 nM mifepristone. To measure cholesterol efflux, mock or ABCA1-transfected cells were incubated with Dulbecco's modified Eagle's medium/bovine serum albumin with or without apoA-I treated under the following conditions:

(1) purified apoA-I was treated for 1 hour with increasing concentrations of HOCl, $H_2O_2$ with MPO plus NACl, ONOO, or $H_2O_2$ with MPO plus $NO_2$;

(2) purified apoA-I was treated for 24 hours with a molar ratio (mol:mol) of 0, 1:25, or 1:50 of acrolein; and (3) peptide 2F was treated for 1 hour with a 25 molar excess of HOCl.

After 2 hour incubations with apoA-I, the medium and cells were assayed for [$^3$H]cholesterol as described in Vaughan, A. M., et al., J. Lipid. Res. 44:1373-1380, 2003. Cholesterol efflux mediated by apoA-I was calculated as the percentage of total [$^3$H]cholesterol (medium plus cells) released into the medium after subtracting the value obtained with Dulbecco's modified Eagle's medium/bovine serum albumin alone. Acrolein adducts of K226 were measured by MS.

Results:

As shown in FIG. 5A, increasing concentrations of HOCl or of $H_2O_2$ with the complete chlorinating MPO system progressively and extensively impaired the cholesterol efflux activity of apoA-I. Moreover, the inhibitory effect observed was proportional to the degree of chlorination of Y192 (shown in FIG. 3A). In contrast, it was unexpectedly observed that MPO-mediated nitration of apoA-I had only a small inhibitory effect on the cholesterol efflux activity of apoA-I as shown in FIG. 5A, despite a similar extent of Y192 modification (shown in FIG. 3B). Finally, as also shown in FIG. 5A, ONOO⁻ had no effect on the cholesterol efflux activity of apoA-I. These results demonstrate that chlorination of apoA-I impairs the efflux activity of apoA-I by a more complex mechanism than the modification of Y192.

As shown in FIG. 5B, treatment of apoA-I with increasing concentrations of acrolein progressively impairs the ability of apoA-I to remove cellular cholesterol by the ABCA1 pathway. This impairment was highly correlated to adduction of K226 (R=0.988), suggesting that modification of lysine K226 plays a role in the impaired function of apoA-I. As shown in FIG. 5C, treatment of the apolipoprotein-mimetic peptide 2F (SEQ ID NO:9) with HOCl significantly reduced its ABCA1 dependent cholesterol efflux activity. This finding raises the concern that D-peptides being developed as therapeutic agents may have markedly reduced potency in atherosclerotic lesions because of oxidative mutations. As shown in TABLE 1, the 2F (SEQ ID NO:9) and 4F (SEQ ID NO:13) peptides contain a KXXY motif that directs tyrosine chlorination through formation of chloramine intermediates. Therefore, it is possible that structural modifications of these peptides disrupt their amphipathic alpha-helical conformation and impair their lipid transport and anti-inflammatory activities. Therefore, oxidation resistant peptides are predicted to maintain potency in the presence of oxidative agents.

Conclusion:

These results strongly suggest that chlorination of Y192 in apoA-I plays a role in impairing the cholesterol efflux activity of apoA-I, but that other mechanisms are also required. This conclusion was supported by a recent study showing that mutating all tyrosines in apoA-I did not prevent the chlorination-induced reduction in cholesterol efflux activity (Peng, D. Q., et al., *J. Biol. Chem.*, 280(40):33775-33784, 2005).

EXAMPLE 5

This Example demonstrates that chlorination of apoA-I reduces amphipathic helices and correlates with the generation of amyloid fibrils.

Circular Dichroism Study

Rationale:

Previous studies have shown that chlorination of apoA-I can reduce its amphipathic helical content (Peng, D. Q., et al., *J. Biol. Chem.* 280(40):33775-33784, 2005). Far UV circular dichroism was used in order to determine if chlorination could generate an unstable form of apoA-I that is subsequently converted into Beta-pleated sheets that could form intermolecular complexes.

Figure 6B:
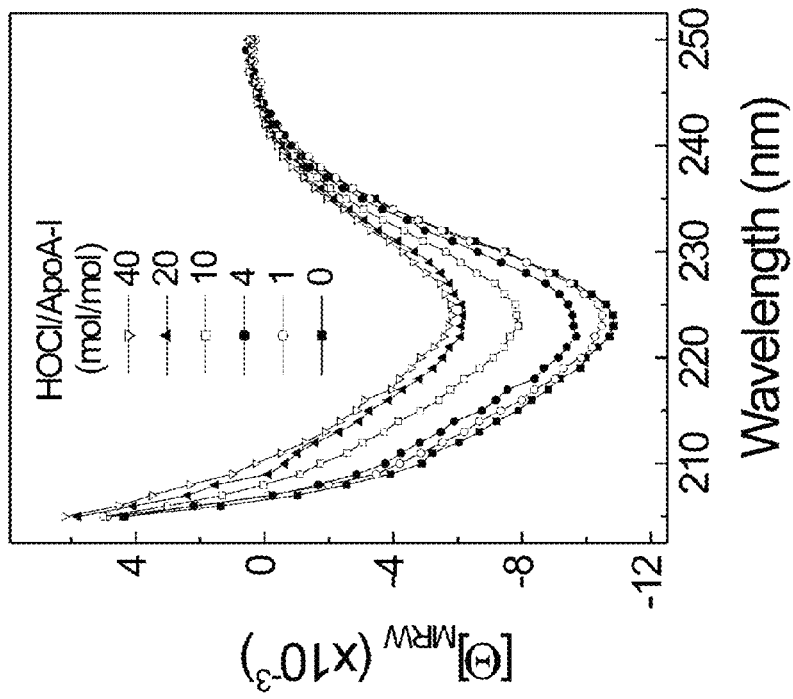
FIG. 6B graphically illustrates a time course of thioflavin T binding to apoA-I after chlorination by HOCl or the MPO system, as described in EXAMPLE 5.
Figure 6A:
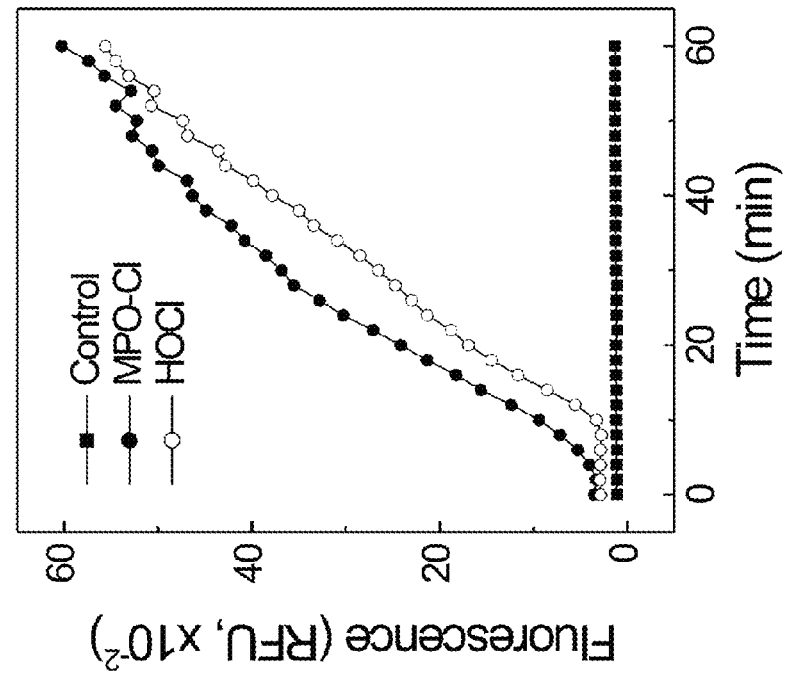
FIG. 6A graphically illustrates that treatment of apoA-I with HOCl causes a concentration-dependent increase in molar ellipticity, as described in EXAMPLE 5.

Methods:

apoA-I was treated for 1 hour with the molar ratio of HOCl as indicated in FIG. 6A. Secondary structure of apoA-I was determined using far UV circular dichroism.

Results:

As shown in FIG. 6A, treatment of apoA-I with HOCl caused a concentration-dependent increase in mean residue molar ellipticity at 222 nm, consistent with a chlorination-induced loss in amphipathic alpha-helix content.

Thioflavin T Binding Study

A thioflavin T binding assay was used to investigate whether chlorination of apoA-I promotes amyloid formation. Thioflavin T is known to bind rapidly to amyloid fibrils and undergoes a dramatic increase in fluorescence at 485 nm upon excitation at 455 nm (see Naiki, H., et al., *Anal. Biochem.* 177:244-249, 1989). apoA-I was chlorinated by treatment with HOCl or the MPO system and a time course of thioflavin T binding to treated apoA-I was carried out over 60 minutes as shown in FIG. 6B.

Results:

As shown in FIG. 6B, chlorination of apoA-I by either HOCl or the complete MPO system markedly increased thioflavin T binding in comparison to untreated apoA-I which had no detectable amyloid-like structures. The appearance of amyloid-like fibrils in chlorinated apoA-I was verified by electron microscopy (data not shown). In contrast, thioflavin T binding assays and electron microscopy failed to reveal amyloid-like structures in nitrated apoA-I.

Discussion:

Taken together, the results shown in FIGS. 6A and 6B strongly suggest that chlorination of apoA-I initiates a conformational switch that impairs its lipid efflux activity, decreases its alpha-helical content, increases its beta-pleated sheet content and promotes formation of complexes and amyloid fibrils. It has been shown that amyloid deposits are commonly associated with atherosclerotic plaques, and that wild-type apoA-I is amyloidogenic in vivo and gives rise to plaque amyloid (Mucchiano, G. I., et al., *J. Pathol.* 193:270-275, 2001). Therefore, these results suggest that modification of specific amino acid residues in apoA-I could play a major role in the formation of amyloid deposits.

EXAMPLE 6

This Example demonstrates that when apoA-I is exposed to HOCl or the MPO system each Met in apoA-I was targeted for oxidation to Met(O).

Rationale:

In order to determine the effect of oxidation of Met residues in apoA-I mediated cholesterol efflux by the ABCA1 pathway, apoA-I was exposed to HOCl or the MPO system and then digested with trypsin or Glu-C and analyzed by LC-ESI-MS/MS.

Methods:

Isolation of MPO, PilB and apoA-I

MPO (EC 1.11.1.7) was isolated from human neutrophils as described in Heinecke, J. W., et al., *J. Biol. Chem.* 268: 4069-4077, 1993. A truncated gene of PilB of *Neisseria gonorrhoeae* expressed in *Escherichia coli* was purified as described in Lowther, W. T., et al., *Proc. Nat'l Acad. Sci.* 97:6463-6468, 2000. apoA-I was dialyzed against 10 mM sodium phosphate buffer (pH 7.4).

Oxidation and Methionine Sulfoxide Reduction Reactions

Oxidation reactions were carried out at 37° C. for 1 h in 10 mM sodium phosphate buffer (pH 7.4) containing 100 uM diethylenetriaminepentaacetic acid (Heinecke, et al., *J. Clin. Invest.* 77:757-761, 1986). For the MPO—$H_2O_2$—Cl— system, the reaction mixture was supplemented with 50 nM MPO and 100 mM NaCl. Oxidized apoA-I (6 uM) was incubated with PilB (4.5:1, apoA-I/enzyme w/w) for 2 h at 37° C. in Tris-HCl buffer (25 mM pH 7.4) containing 15 mM dithiothreitol (Brot, N., et al., *Methods Enzymol.* 107:352-360, 1984).

Liquid Chromatography Electrospray Ionization Mass Spectrometry (LC-ESI-MS)

apoA-I was incubated overnight at 37° C. with sequencing grade modified trypsin (20:1, protein/enzyme, w/w) or with endoproteinase Glu-C (*Staphylococcus aureus* V8: 10:1, protein/enzyme, w/w) in 100 mM $NH_4HCO_3$, pH 7.8. Digestion was halted by acidification (pH 2-3). LC-ESI-MS analyses were performed in the positive ion mode with a Finnigan Mat LCQ ion trap instrument (San Jose, Calif.) coupled to a Waters 2690 HPLC system. Peptide digests were separated on a reverse-phase column (Vydac C18 MS column) and subjected to MS and MS/MS analysis as described in Shao, B., et al., *J. Biol. Chem.* 279:7856-7866, 2004; and Shao, B., et al., *J. Biol. Chem.* 280:36386-36396, 2005.

Figure 7A:
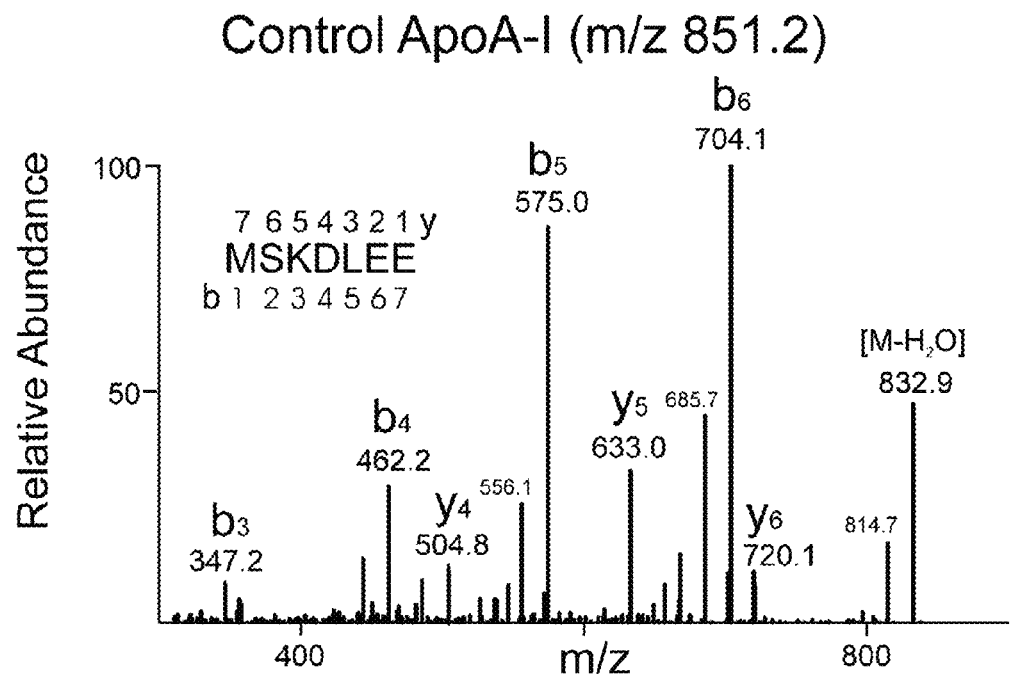
FIG. 7A illustrates a representative analysis of a tryptic digest of untreated apoA-I protein analyzed by LC-ESI-MS/MS, wherein the peptide "MSKDLEE" corresponds to amino acid positions 86 to 92 of SEQ ID NO:3, as described in EXAMPLE 6.
Figure 7B:
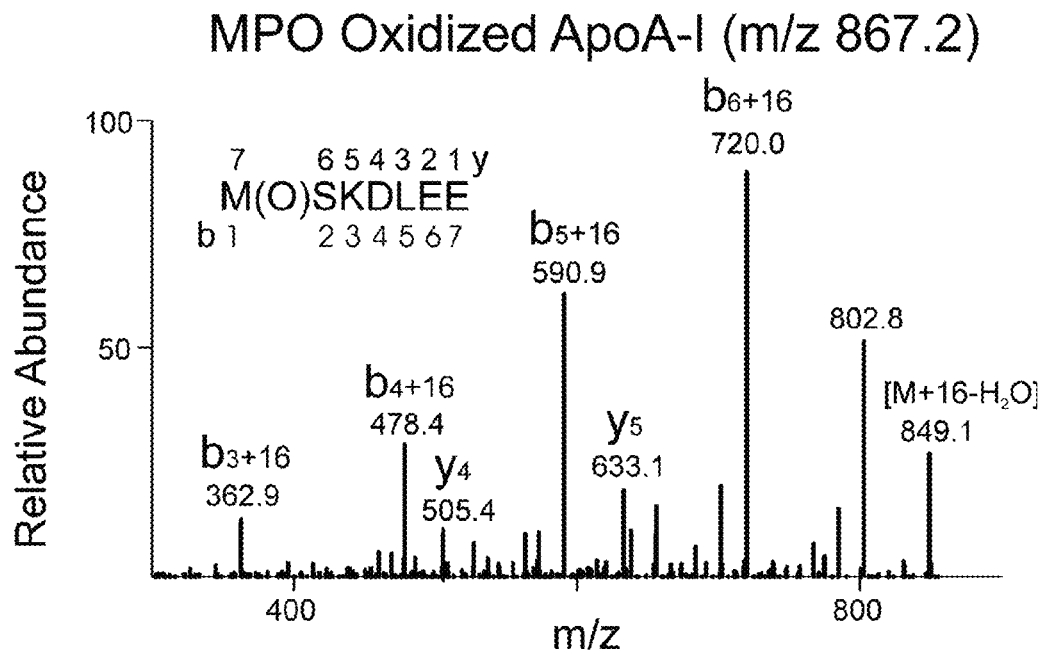
FIG. 7B illustrates a representative analysis of a tryptic digest of apoA-I treated with the MPO—H2O2—Cl system and analyzed by LC-ESI-MS/MS, demonstrating that Met86, Met112, and Met148 were targeted for oxidation, wherein the peptide "MSKDLEE" corresponds to amino acid positions 86 to 92 of SEQ ID NO:3, as described in EXAMPLE 6.
Figure 7C:
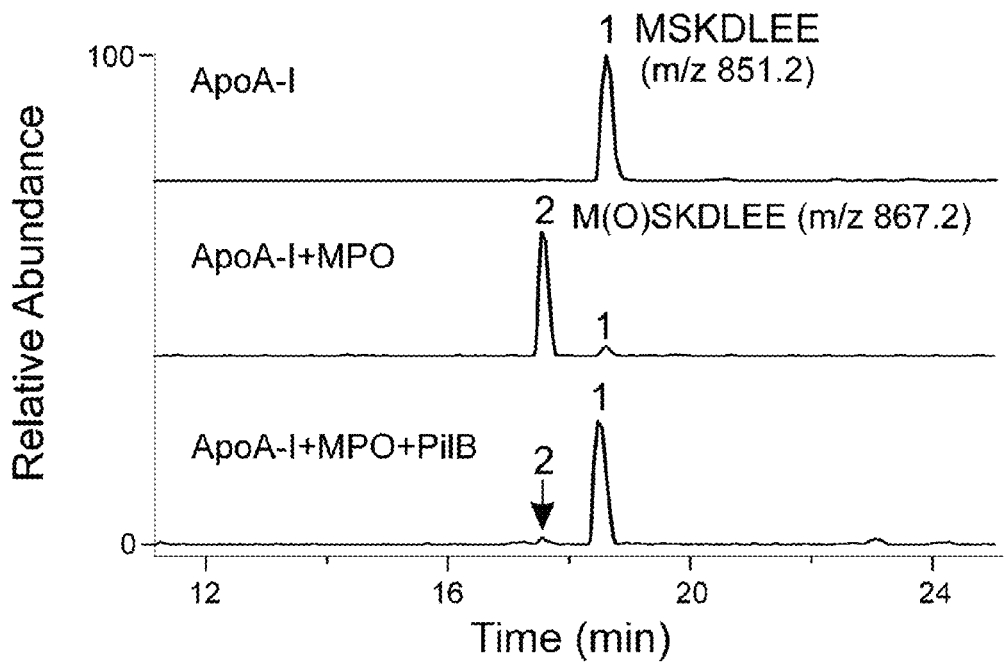
FIG. 7C illustrates a selective ion chromatogram comparing the Met86 residue of untreated apoA-I, after treatment with MPO, and after treatment with MPO plus PilB, wherein the peptide "MSKDLEE" corresponds to amino acid positions 86 to 92 of SEQ ID NO:3, as described in EXAMPLE 6.

Results:

As shown in FIG. 7A and FIG. 7B, LC-ESI-MS/MS analysis demonstrates that each of the three Met residues in apoA-I (Met86, Met112, and Met148) had been targeted for oxidation to Met(O) in the presence of HOCl or MPO. As shown in FIG. 7C, when apoA-I was first exposed to the complete MPO system and then incubated with the methionine sulfoxide reductase PilB, Met(O) was converted back to methionine.

EXAMPLE 7

This Example demonstrates that the combined effects of chlorination of Tyr192 and oxidation of Met residues in apoA-I account for the reduced ability of apoA-I to promote cholesterol efflux by the ABCA1 pathway.

Methods:

Mutation of apoA-I

A Tyr192Phe mutant of apoA-I was introduced within human apoA-I cDNA by primer directed PCR mutagenesis or by the Mega-primer method and expressed using the pNFXex bacterial expression vector (see Oda, M. N., et al., *Biochemistry* 40:1710-1718, 2001; and Kammann, M., et al., *Nucleic Acid Res.* 17:5404, 1989). All mutations were verified by dideoxy automated fluorescent sequence analysis.

Efflux of Cellular Cholesterol

BHK cells transfected with a mifepristone-inducible GeneSwitch (Invitrogen) system containing a human ABCA1 cDNA were incubated with serum-free medium with or without 10 nM mifipristone for 24 h to generate cells expressing virtually no or high levels of ABCA1, respectively (see Vaughan, A. M., and J. F. Oram, *J. Lipid Res.* 44:1373-1380, 2003). To radiolabel cellular cholesterol, [$^3$H]cholesterol was added to the acetyl LDL medium for macrophages and the growth medium prior to ABCA1 induction for BHK cells. Efflux of [$^3$H]cholesterol was measured after a 2 h incubation in medium with or without apoA-I (Tang, C., et al., *J. Biol. Chem.* 279:7622-7628, 2004).

Results:

An engineered Tyr192Phe mutant of apoA-I was incubated in the presence of HOCl, and ESI-MS analysis confirmed that HOCl fails to chlorinate Phe192 of this mutant protein (data not shown). The ability of apoA-I and the Tyr192Phe mutant apoA-I were tested for the ability to promote cholesterol efflux from ABCA1-transfected BHK cells. As shown in FIG. 8A, the rates of cholesterol efflux were virtually identical as concentrations of the native apoA-I and Tyr192Phe mutant apoA-I protein increased, indicating that substituting Phe for Tyr has little effect on the biological activity of the apolipoprotein.

Figure 9A:
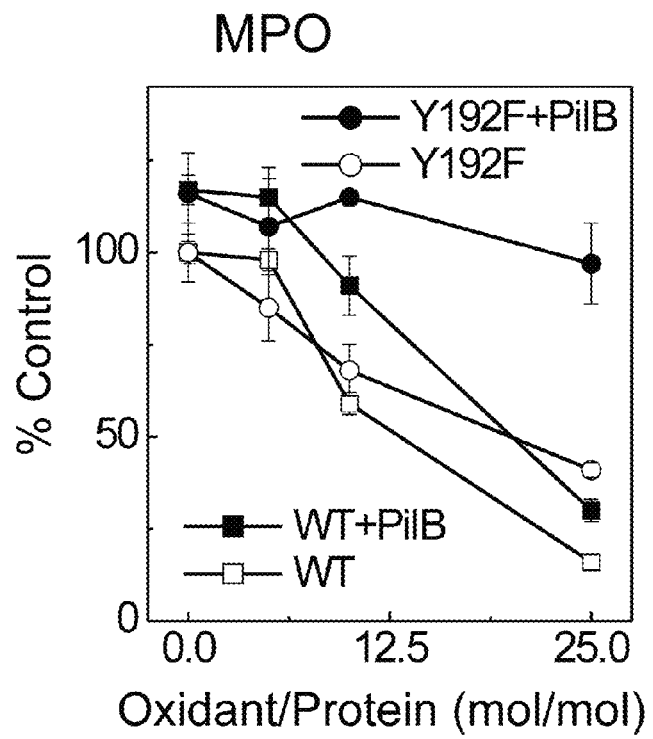
FIG. 9A graphically illustrates the effect of treatment with increasing concentrations of MPO and $H_2O_2$ on wild type apoA-I, Y192F mutant apoA-I, either with or without treatment with PilB (to reduce Met(O) back to Met) as described in EXAMPLE 8.
Figure 9B:
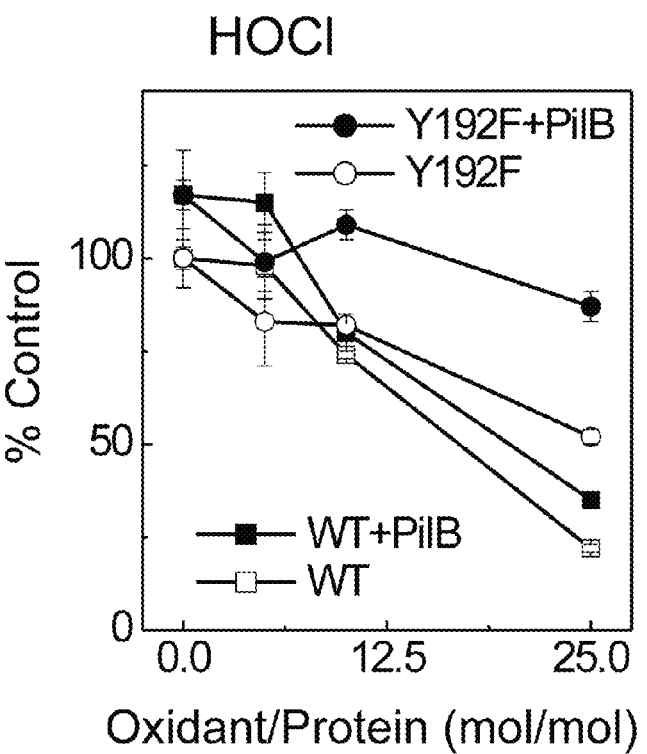
FIG. 9B graphically illustrates the effect of treatment with increasing concentrations of HOCl on wild type apoA-I, Y192F mutant apoA-I, either with or without treatment with PilB (to reduce Met(O) back to Met), as described in EXAMPLE 8.

The effect of oxidation on the ability of apoA-I and tyr192Phe apoA-I to remove cholesterol from cells by the ABCA1 pathway was determined by exposure to the MPO system. It was observed that oxidation by the MPO system significantly decreased the cholesterol efflux promoted by apoA-I or Tyr192Phe apoA-I (FIG. 8B and FIG. 9A). However, the mutant protein appeared somewhat resistant to oxidative inactivation by MPO when the concentration of $H_2O_2$ was high. Similar results were observed when apoA-I was directly oxidized with HOCl (FIG. 9B).

After apoA-I was exposed to the complete MPO system with increasing $H_2O_2$ concentrations (FIG. 9A) or increasing HOCl concentrations (FIG. 9B), incubating apoA-I with PilB to reduce Met(O) back to Met partially restored its ability to promote cholesterol efflux at all oxidant concentrations. Similar partial protective effects of the Tyr192Phe substitution or methionine sulfoxide reduction were observed when cellular cholesterol efflux was monitored over a range of apoA-I concentrations (FIG. 8B). Thus, neither inhibition of Tyr192 chlorination nor reduction of Met(O) alone markedly protected apoA-I from oxidative inactivation.

The effect of a combination of a Tyr192Phe apoA-I mutation and Met(O) reduction was then tested for the ability to promote cholesterol efflux by the ABCA1 pathway after exposure to MPO. As shown in FIG. 9A, it was unexpectedly observed that when the mutant Tyr192Phe apoA-I protein was first exposed to increasing $H_2O_2$ concentrations in the complete MPO system and then incubated with PilB, its ability to promote cholesterol efflux was nearly the same as that of native apoA-I. This result was also observed at low concentrations of apoA-I (FIG. 8B). Similar results were obtained after exposing the Tyr192Phe mutant to HOCl followed by incubation with PilB (FIG. 9B). These observations strongly suggest that two oxidation events: (1) chlorination of Tyr192; and (2) oxidation of one or more Met residues, account for most of the decrease in the ability of apoA-I to promote cholesterol efflux by the ABCA1 pathway.

EXAMPLE 8

This Example describes an animal model that may be used to test candidate ApoA-I polypeptides.

Methods:

An LDL receptor -/- (LDLR-/-) mouse model in which mice lack or express MPO in their macrophages, will be utilized, produced as described in McMillen, T. S., et al., *Circulation* 111:2798-2804, 2005, incorporated herein by reference. It has previously been shown that MPO expression in LDLR-/- mice fed the Western diet increases atherosclerosis (see McMillen, T. S., et al., supra).

In order to ensure that the apoA-I polypeptides are absorbed and stable, an initial control study will be conducted in which the polypeptide will be iodinated and administered to mice by oral gavage, followed by HPLC measurement of the serum content of radiolabeled intact polypeptide after 4 and 8 hours.

The oxidation resistant apoA-I polypeptides and/or apoA-I peptide mimetics, along with a set of corresponding controls will be administered to mice, following the protocol described in Navab, et al., *Circulation* 105:290-292, 2002. In brief, mice will be fed an atherogenic Western diet for 6 weeks, and vehicle control, oxidation resistant mutant apoA-I polypeptides (e.g., HOCl/acrolein-resistant) and wild-type oxidation sensitive control polypeptides will be administered to mice for 6 weeks. Peptides composed of D-amino acid peptides can be administered by including the polypeptides in the drinking water at a concentration of about 50 µg/ml (typically mice consume about 2.5 ml of water per day). ApoA-I and peptides composed of L-amino acids will be injected into the mice over the six week time period. Water consumption will be monitored using graduated water bottles. At least 10 female mice will be used per group. Plasma lipid and lipoprotein levels will be measured using standard enzymatic assays.

After the administration of oxidation resistant mutant apoA-I polypeptides, structural and functional analysis will be conducted on polypeptides isolated from atherosclerosis lesions in the mice. Conventional biochemical techniques such as size exclusion, ion exchange chromatography and HPLC will be used followed by MS analysis to determine the structural modifications of the administered polypeptides that occur in the lesions of the mice. In addition, atherosclerotic lesion area will be quantified in the treated mice using the methods described in Schreyer, S. A., et al., *J. Biol. Chem.* 271:26174-26178, 1996, incorporated herein by reference. It is expected that the atherogenic effects of the Western diet in LDLR–/– mice will be reduced in the mice that receive an effective dose of the oxidation-resistant apoA-I polypeptides described herein.

EXAMPLE 9

This Example demonstrates that oxidation of apoA-I with MPO causes loss of its ability to activate Lecithin Cholesterol Acyltransferase ("LCAT"), a key enzyme in promoting cholesterol efflux from lipid-loaded macrophages (Curtiss, L. K., et al., *Arterioscler. Thromb. Vasc. Biol.* 26(1):12-19, 2006), and that this is associated with oxidation of Met148. Thus, conservative substitutions of this amino acid or other oxidation sensitive amino acid residues in apoA-I may improve the ability of apoA-I to prevent atherosclerosis.

Methods:

Isolation of HDL

Blood was collected from healthy subjects who had fasted overnight and was anticoagulated with EDTA. HDL (density 1.125 g/ml-1.210 g/ml) was prepared from plasma by sequential ultracentrifugation and was depleted of apolipoproteins E and B 100 by heparin-agarose chromatography.

HOCl Modification

Reactions with isolated HDL (1 mg protein/ml) were carried out at 37° C. for 1 h in 50 mM sodium phosphate buffer (pH 7.4) containing 100 uM DTPA and 100 nM MPO. Reactions were initiated by adding hydrogen peroxide and terminated by adding a 20-fold molar excess (relative to peroxide) of Met.

Proteolytic Digestion

Native or MPO-modified HDL was incubated overnight at 37° C. with a 20:1 ratio (w/w) of endoproteinase Glu-C (from *Staphylococcus aureus* V8), sequencing grade modified trypsin (Promega, Madison, Wis.), or Glu-C/trypsin in 50 mM $NH_4HCO_3$ (pH 7.8). Digestion was halted by acidifying (pH 2-3) with trifluoroacetic acid. LC-ESI-MS analysis was performed as described in Shao, B., et al., *J. Biol. Chem.* 280(43):3686-3696, 2005, which is incorporated by reference.

Results:

As shown in FIGS. 7A and 7B, MS/MS analysis of Glu-C digest or tryptic digests of MPO-modified HDL-associated apoA-I indicated that all 3 Methionine residues of apoA-I were modified, but with different sensitivities to the concentration of peroxide in the reaction mixture.

Figure 7D:
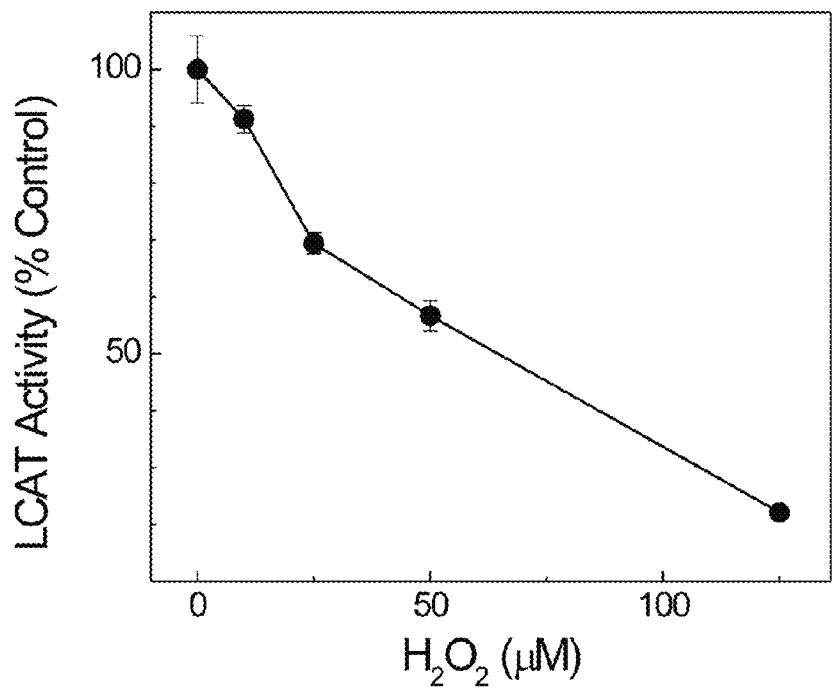
FIG. 7D graphically illustrates that oxidation of apoA-I with MPO causes loss of its ability to activate Lecithin Cholesterol Acyltransferase ("LCAT"), a key enzyme in promoting cholesterol efflux from lipid-loaded macrophages, as described in EXAMPLE 9.
Figure 7E:
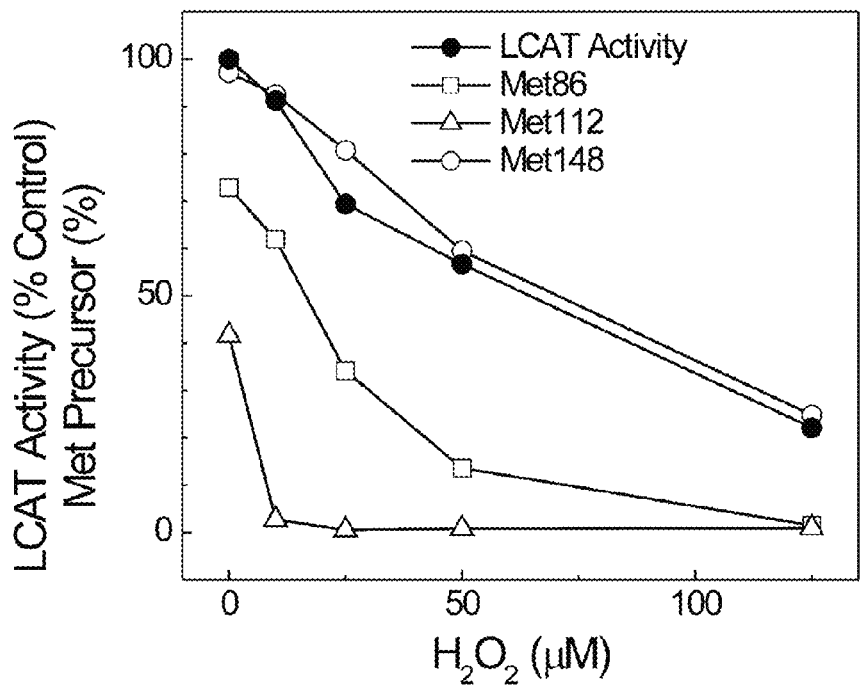
FIG. 7E graphically illustrates that the oxidative loss of Met148 in apoA-I exposed to MPO is quantitatively associated with inhibition of LCAT activity, as described in EXAMPLE 9.

As shown in FIG. 7D, apoA-I exposed to MPO looses its ability to activate LCAT, and as shown in FIG. 7E, the oxidative loss of Met148 is quantitatively associated with inhibition of LCAT activity.

EXAMPLE 10

This Example demonstrates that treatment of apoA-I with MDA predominately modifies Lys12, Lys 118, Lys133, Lys195, Lys206, Lys226, Lys238 and Lys239, and that this is associated with loss of ABCA1 activity of the modified apoA-I.

Methods:

Isolation of HDL and apoA-I

Blood was collected from healthy subjects who had fasted overnight and was anticoagulated with EDTA. HDL (density 1.125 g/ml-1.210 g/ml) was prepared from plasma by sequential ultracentrifugation and was depleted of apolipoproteins E and B 100 by heparin-agarose chromatography. ApoA-I was purified to apparent homogeneity from HDL.

Acrolein Modification

Reactions with isolated apoA-I (25 uM, 0.7 mg protein/ml) were carried out at 37° C. for 24 h in 50 mM sodium phosphate buffer (pH 7.4) containing 100 uM DTPA. Reactions were initiated by adding MDA and terminated by adding a 20-fold molar excess (relative to MDA) of aminoguanidine.

Proteolytic Digestion

Native or acrolein-modified apoA-I was incubated overnight at 37° C. with a 20:1 ratio (w/w) of endoproteinase Glu-C (from *Staphylococcus aureus* V8), sequencing grade modified trypsin (Promega, Madison, Wis.), or Glu-C/trypsin in 50 mM $NH_4HCO_3$ (pH 7.8). Digestion was halted by acidifying (pH 2-3) with trifluoroacetic acid. LC-ESI-MS analysis was performed as described in Shao, B., et al., *J. Biol. Chem.* 280(43):3686-3696, 2005, which is incorporated by reference.

Figure 4C:
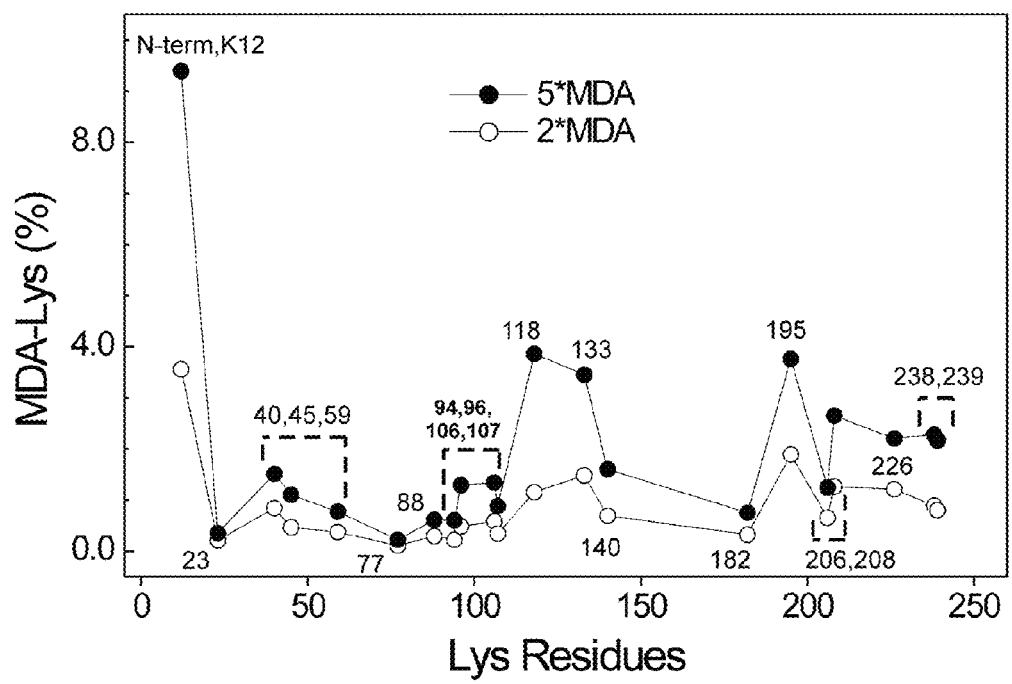
FIG. 4C graphically illustrates the selective modification of residues Lys12, Lys118, Lys133, Lys195, Lys206, Lys 226, Lys238, and Lys 239 by increasing molar ratios (mol MDA/mol apoA-I) of malondialdehyde (MDA), a reactive carbonyl generated by lipid peroxidation, to 2*MDA and 5*MDA (a molar ratio of MDA to apoA-I of 2 and 5, respectively), as described in EXAMPLE 10.
Figure 4D:
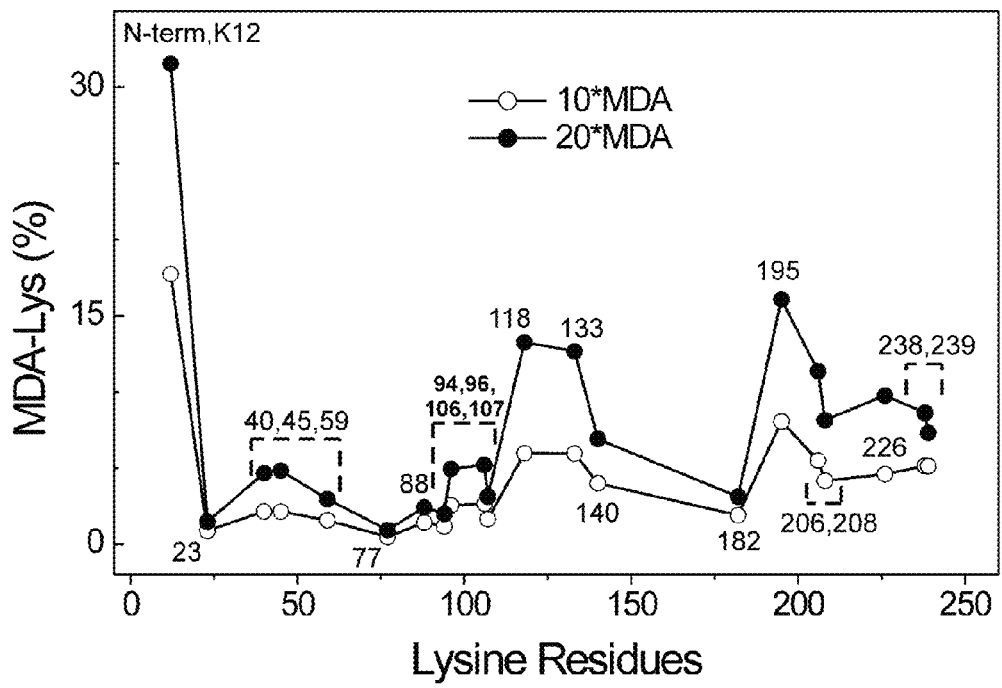
FIG. 4D graphically illustrates the selective modification of residues Lys12, Lys118, Lys133, Lys195, Lys206, Lys 226, Lys238, and Lys 239 by increasing molar ratios (mol MDA/mol apoA-I) of malondialdehyde (MDA), a reactive carbonyl generated by lipid peroxidation, to 10*MDA and 20*MDA ( a molar ratio of MDA to apoA-I of 10 and 20), as described in EXAMPLE 10.

Results:

FIGS. 4C and 4D graphically illustrate the selective modification of residues Lys12, Lys118, Lys133, Lys195, Lys206, Lys 226, Lys238, and Lys 239 by increasing molar ratios (mol MDA/mol apoA-I) of malondialdehyde (MDA), a reactive carbonyl generated by lipid peroxidation. 2*MDA, 5*MDA, 10*MDA and 20*MDA indicate a molar ratio of MDA to ApoA-I of 2, 5, 10, and 20 respectively. As shown in FIGS. 4C and 4D, MS/MS analysis of Glu-C digest or tryptic digests of MDA-modified apoA-I indicated that only a subset of lysine residues in apoA-I (Lys12, Lys 118, Lys133, Lys195, Lys206, Lys226, Lys238 and Lys239) were modified in high yield.

Figure 4E:
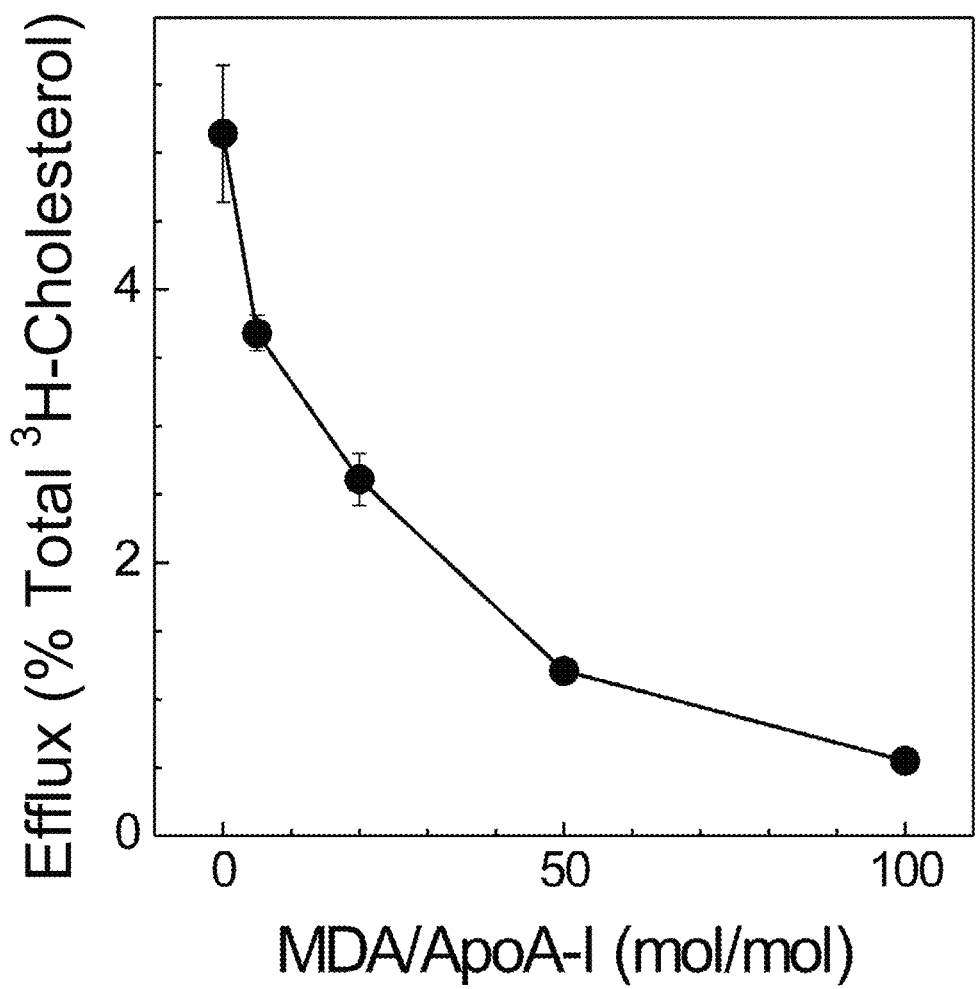
FIG. 4E graphically illustrates the effect of treatment of isolated apoA-I with MDA, wherein increasing concentrations of MDA progressively and extensively impaired the cholesterol efflux activity of apoA-I, and the reduction in efflux activity was proportional to the degree of modification of residues Lys12, Lys118, Lys133, Lys 195, Lys206, Lys226, Lys238 and Lys239, as described in EXAMPLE 10.

FIG. 4E graphically illustrates the effect of treatment of isolated apoA-I with MDA, wherein increasing concentrations of MDA progressively and extensively impaired the cholesterol efflux activity of apoA-I, and the reduction in efflux activity was proportional to the degree of modification of residues Lys12, Lys118, Lys133, Lys 195, Lys206, Lys226, Lys238 and Lys239. Therefore, as shown in FIG. 4E, the loss of lysine residues in apoA-I is quantitatively associated with inhibition of ABCA1 activity. This observation is likely to have therapeutic significance because it has also been observed in immunohistochemical studies that MDA adducts are present in animal and human atherosclerotic lesions, as reviewed in Witztum, J. L., and D. Steinberg, "Role of Oxidized Low Density Lipoprotein in Atherogenesis," *J. Clin. Invest.* 88(6):1785-1792, 1991.

EXAMPLE 11

This Example demonstrates that site-specific oxidation of tyrosines in amphipathic alpha-helices can impair their lipid transport activities.

Methods:

Baby Hamster Kidney (BHK) cells were transfected with a cDNA expressing ABCA1 (ABCA1) or with a transfection vector alone (Mock). The transfected cells were radiolabeled with $^3$H-cholesterol, washed and then incubated for 4 hours with media containing 20 µg/ml untreated or HOCl-treated (5 molar ratio HOCl to peptide) peptide 2F (SEQ ID NO:9). At the end of the incubation, the amount of $^3$H-cholesterol (efflux) released from the cells was measured and expressed as the percent total (media plus cells) $^3$H-cholesterol.

Figure 9C:
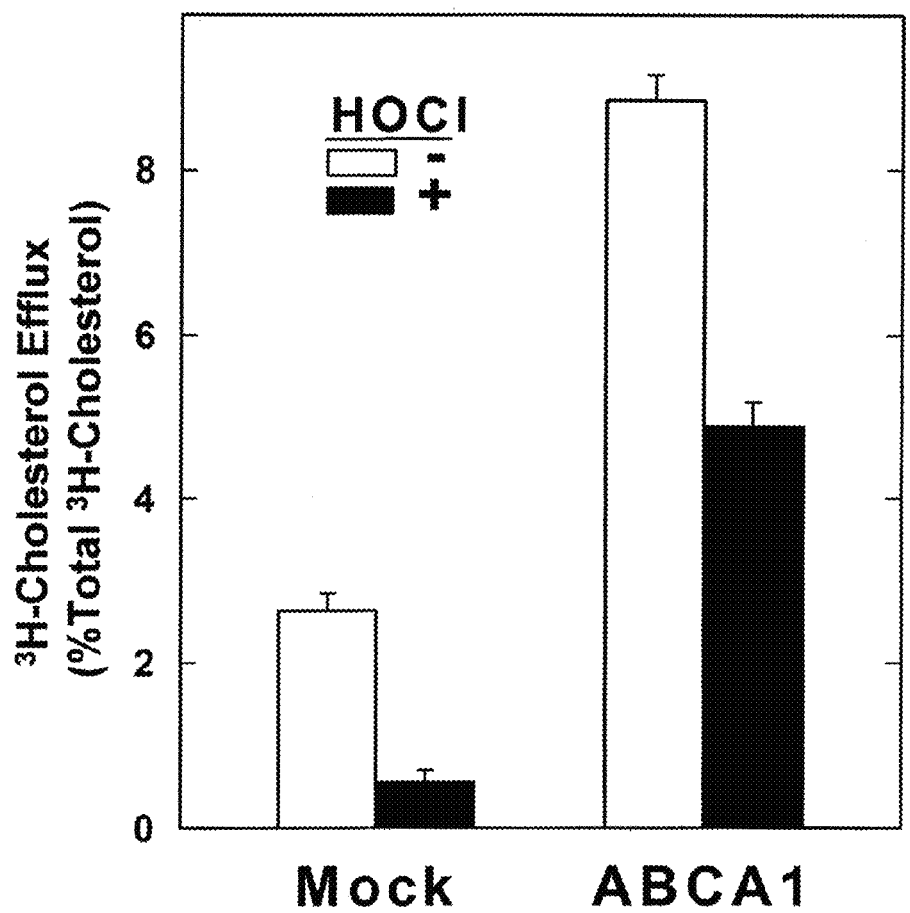
FIG. 9C graphically illustrates that treatment of acetyl-18A-NH2 ("2F") (SEQ ID NO:9) with HOCl significantly reduced the ability of 2F to remove cholesterol by both the ABCA1-independent and dependent mechanisms, indicating that site-specific oxidation of tyrosines in amphipathic alpha-helices can impair their lipid transport activities, as described in EXAMPLE 11.

Results:

As shown in FIG. 9C, the treatment of the 2F peptide (SEQ ID NO:9, shown in TABLE 1) with HOCl significantly reduced the ability of 2F (SEQ ID NO:9) to remove cholesterol by both the ABCA1-independent and ABCA1-dependent mechanisms. As described herein, the 2F peptide is an 18 amino acid analog of the type of amphipathic alpha-helices found in apolipoproteins. These studies indicate that site-specific oxidation of tyrosines in amphipathic alpha-helices such as 2F can impair their lipid transport activities.

While illustrative embodiments have been illustrated and described, it will be appreciated that various changes can be made therein without departing from the spirit and scope of the invention.

The embodiments of the invention in which an exclusive property or privilege is claimed are defined as follows:

1. An isolated oxidation resistant mutant apolipoprotein A-I (apoA-I) polypeptide comprising:
   an amino acid sequence having at least 85% amino acid sequence identity to the amino acid sequence of SEQ ID NO:4, the mutant apoA-I polypeptide comprising a combination of:
   (1) a conservative amino acid substitution at the residue corresponding to Tyr192 of the amino acid sequence of SEQ ID NO:3; and
   (2) at least one conservative amino acid substitution at the residue corresponding to Met86, Met112, or Met148 of the amino acid sequence of SEQ ID NO:3,
   wherein the oxidation resistant mutant apoA-I polypeptide is more resistant to modification by an oxidizing agent as compared to an apoA-I polypeptide comprising the amino acid sequence of SEQ ID NO:3 and interacts with ATP-binding cassette transporter A1 (ABCA1) and promotes ABCA1-mediated cholesterol efflux activity.

2. The isolated oxidation resistant mutant apoA-I polypeptide of claim 1, wherein the polypeptide has at least 90% amino acid sequence identity to the amino acid sequence of SEQ ID NO:4.

3. The isolated oxidation resistant mutant apoA-I polypeptide of claim 1, wherein the polypeptide has at least 90% amino acid sequence identity to the amino acid sequence of SEQ ID NO:3.

4. The isolated oxidation resistant mutant apoA-I polypeptide of claim 1, wherein the polypeptide comprises the amino acid sequence of SEQ ID NO:5, wherein at least one of Xaa at positions 86, 112, and 148 of the amino acid sequence of SEQ ID NO:5 is Leu.

5. The isolated oxidation resistant mutant apoA-I polypeptide of claim 1, wherein the polypeptide comprises the amino acid sequence of SEQ ID NO:6, wherein at least one of Xaa at positions 43, 69, and 104 of the amino acid sequence of SEQ ID NO:6 is Leu.

6. The isolated oxidation resistant mutant apoA-I polypeptide of claim 1, wherein the polypeptide comprises at least two conservative amino acid substitutions at the residues corresponding to Met86, Met112, and Met148 of the amino acid sequence of SEQ ID NO:3.

7. The isolated oxidation resistant mutant apoA-I polypeptide of claim 1, wherein the at least one conservative amino acid substitution at the residue corresponding to Met86, Met112, or Met148 of the amino acid sequence of SEQ ID NO:3 is with Leu.

8. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitution at the residue corresponding to Met86 of the amino acid sequence of SEQ ID NO:3 is with Leu.

9. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitution at the residue corresponding to Met112 of the amino acid sequence of SEQ ID NO:3 is with Leu.

10. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitution at the residue corresponding to Met148 of the amino acid sequence of SEQ ID NO:3 is with Leu.

11. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitutions at the residues corresponding to Met86 and Met112 of the amino acid sequence of SEQ ID NO:3 are with Leu.

12. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitutions at the residues corresponding to Met86 and Met148 of the amino acid sequence of SEQ ID NO:3 are with Leu.

13. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitutions at the residues corresponding to Met112 and Met148 of the amino acid sequence of SEQ ID NO:3 are with Leu.

14. The isolated oxidation resistant mutant apoA-I polypeptide of claim 6, wherein the conservative amino acid substitution at the residue corresponding to Tyr192 of the amino acid sequence of SEQ ID NO:3 is with Phe and the conservative amino acid substitutions at the residues corresponding to Met86, Met112, and Met148 of the amino acid sequence of SEQ ID NO:3 are with Leu.

15. The isolated oxidation resistant mutant apoA-I polypeptide of claim 1, further comprising a conservative amino acid substitution at the residue corresponding to Lys226 of the amino acid sequence of SEQ ID NO:3.

16. A method of producing the oxidation resistant mutant apoA-I polypeptide of claim 1, the method comprising:
   (1) introducing a conservative amino acid substitution at the residue corresponding to Tyr192 of the amino acid sequence of SEQ ID NO:3 in an amino acid sequence having at least 85% amino acid sequence identity to the amino acid sequence of SEQ ID NO:3 or SEQ ID NO:4; and
   (2) introducing at least one conservative amino acid substitution at the residue corresponding to Met86, Met112, or Met148 of the amino acid sequence of SEQ ID NO:3 in the amino acid sequence having at least 85% amino acid sequence identity to the amino acid sequence of SEQ ID NO:3 or SEQ ID NO:4,
   thereby producing the oxidation resistant mutant apoA-I polypeptide of claim 1, wherein the oxidation resistant mutant apoA-I polypeptide is more resistant to modification by an oxidizing agent as compared to an apoA-I polypeptide comprising the amino acid sequence of SEQ ID NO:3 and interacts ABCA1 and promotes ABCA1-mediated cholesterol efflux activity.

* * * * *